(12) United States Patent
Zhang et al.

(10) Patent No.: US 10,444,050 B2
(45) Date of Patent: Oct. 15, 2019

(54) LIQUID SUPPLYING SYSTEM AND METHOD FOR DRIVING SAME

(71) Applicant: SARAYA CO., LTD., Osaka-shi, Osaka (JP)

(72) Inventors: Haijun Zhang, Shandong (CN);
Qinghai Zhao, Shandong (CN);
Jianglong Yu, Shandong (CN);
Tomomasa Itarashiki, Osaka (JP);
Daiki Anraku, Osaka (JP)

(73) Assignee: Saraya Co., Ltd., Osaka-shi, Osaka (JP)

( * ) Notice: Subject to any disclaimer, the term of this patent is extended or adjusted under 35 U.S.C. 154(b) by 0 days.

(21) Appl. No.: 16/061,788

(22) PCT Filed: Dec. 8, 2016

(86) PCT No.: PCT/JP2016/086608
§ 371 (c)(1),
(2) Date: Jun. 13, 2018

(87) PCT Pub. No.: WO2017/104543
PCT Pub. Date: Jun. 22, 2017

(65) Prior Publication Data
US 2018/0364085 A1     Dec. 20, 2018

(30) Foreign Application Priority Data

Dec. 14, 2015    (JP) ................................ 2015-243578

(51) Int. Cl.
*A61L 2/08*       (2006.01)
*A61L 9/00*       (2006.01)
(Continued)

(52) U.S. Cl.
CPC ................ *G01F 11/28* (2013.01); *A61L 2/24* (2013.01); *B01J 4/02* (2013.01); *A61L 2/20* (2013.01)

(58) Field of Classification Search
CPC ...... A61L 2/00; A61L 2/0088; A61L 2202/15; B05C 7/00; B67D 1/00
(Continued)

(56) References Cited

U.S. PATENT DOCUMENTS

2013/0094995 A1     4/2013    Koyama

FOREIGN PATENT DOCUMENTS

EP         2578240 A1 *   4/2013  ............... A61L 2/20
FR           981173 A       5/1951
(Continued)

OTHER PUBLICATIONS

International Search Report (PCT/ISA/210) dated Mar. 7, 2017, by the Japan Patent Office as the International Searching Authority for International Application No. PCT/JP2016/086608.
(Continued)

*Primary Examiner* — Monzer R Chorbaji
(74) *Attorney, Agent, or Firm* — Buchanan Ingersoll & Rooney PC

(57) ABSTRACT

Provided is a system for supplying a liquid (such as an irritative chemical solution) safely. This liquid supplying system comprises: (a) a means that creates a negative pressure in a treatment chamber by driving a first depressurizing means and depressurizing the treatment chamber; (b) a means that introduces the negative pressure of the treatment chamber to a measurement chamber; (c) a means that maintains the negative pressure introduced to the measurement chamber; (d) a means that sucks a liquid from a container into the measurement chamber by employing the negative pressure of the measurement chamber; and (e) a
(Continued)

means that sucks the liquid of the measurement chamber into the treatment chamber by employing a vacuum in the treatment chamber.

10 Claims, 16 Drawing Sheets

(51) Int. Cl.
    *A61L 2/00*      (2006.01)
    *B08B 7/00*      (2006.01)
    *B08B 5/04*      (2006.01)
    *B08B 9/00*      (2006.01)
    *G01F 11/28*      (2006.01)
    *A61L 2/24*      (2006.01)
    *B01J 4/02*      (2006.01)
    *A61L 2/20*      (2006.01)

(58) Field of Classification Search
    USPC ........... 422/1, 26, 28, 31, 33, 292, 305, 307; 134/6, 21, 22.1
    See application file for complete search history.

(56) References Cited

FOREIGN PATENT DOCUMENTS

| | | |
|---|---|---|
| JP | 52-119352 A | 10/1977 |
| JP | H09-131390 A | 5/1997 |
| JP | 2012-101328 A | 5/2012 |
| JP | 2013-90908 A | 5/2013 |
| WO | 2011/038487 A1 | 4/2011 |

OTHER PUBLICATIONS

Written Opinion (PCT/ISA/237) dated Mar. 7, 2017, by the Japan Patent Office as the International Searching Authority for International Application No. PCT/JP2016/086608.

International Preliminary Report on Patentability issued in corresponding PCT Application No. PCT/JP2016/086608, dated June 28, 2018, (9 pages).

* cited by examiner

LIQUID SUPPLYING SYSTEM AND METHOD FOR DRIVING SAME

TECHNICAL FIELD

The present invention relates to a system supplying a liquid and a method for driving the same. The present invention particularly relates to a system safely and reliably supplying a liquid (e.g., a chemical liquid) contained in a container and a method for driving the same.

BACKGROUND ART

A sterilization apparatus using a liquid such as peracetic acid is disclosed in Patent Document 1 (WO 2011/038487). The liquid used in this type of apparatus has a strong stimulant action and may cause inflammation when coming into contact with the skin. Therefore, a liquid supplying apparatus is preferably designed such that a chemical agent is prevented from coming into contact with the skin. Additionally, it is desirable that the liquid is accurately measured.

PRIOR ART DOCUMENT

Patent Document

Patent Document 1: WO 2011/038487

SUMMARY OF THE INVENTION

Problem to be Solved by the Invention

An object of the present invention is to provide a novel liquid supplying system capable of accurately measuring an amount of liquid to be supplied and a method for driving the same.

Means for Solving Problem

A preferable embodiment of a liquid supplying system according to the present invention comprises
a processing chamber (121) having a space (122) of a predetermined volume;
a first depressurizing means (123) depressurizing the space (122) of the processing chamber (121);
a container (20) containing a liquid;
a measuring chamber (151) measuring the liquid;
a first passage (111) connecting the container (20) and the processing chamber (121) through the measuring chamber (151);
a first valve (131) disposed on the first passage (111) between the container (20) and the measuring chamber (151);
a second valve (132) disposed on the first passage (111) between the measuring chamber (151) and the processing chamber (121); and
a control part (90) controlling the depressurizing means (123), the first valve (131), and the second valve (132), wherein
the control part (90) includes
a) a first means executing a first process of driving the first depressurizing means to depressurize the processing chamber so as to form a negative pressure in the processing chamber with the second valve closed,
b) a second means executing a second process of opening the second valve with the first valve closed so as to introduce the negative pressure of the processing chamber into the measuring chamber,
c) a third means executing a third process of closing the second valve with the first valve closed so as to retain the negative pressure introduced into the measuring chamber,
d) a fourth means executing a fourth process of opening the first valve with the second valve closed so as to suck the liquid from the container into the measuring chamber by using the negative pressure of the measuring chamber,
e) a fifth means executing a fifth process of opening the second valve with the first valve closed so as to suck the liquid in the measuring chamber into the processing chamber by using a vacuum in the processing chamber.

Another form of the liquid supplying system according to the present invention comprises
a branching portion (141) disposed on the first passage (111) between the container (20) and the first valve (131),
a second passage (112) having one end connected to the branching portion (141),
a second depressurizing means (153) connected to the other end of the second passage (112), and
a temporary storage chamber (154) and a third valve (133) disposed on the second passage (112) in order from the one end toward the other end, and
the liquid supplying system comprises
f) a sixth means executing a sixth process of driving the second depressurizing means with the third valve opened before execution of the first process so as to suck the liquid into the second passage portion from the container to the temporary storage chamber.

Another form of the liquid supplying system according to the present invention comprises a seventh means executing a seventh process of returning to the container (20) the liquid remaining in the second passage portion from the container (20) to the third valve (133) after the fifth process.

Another form of the liquid supplying system according to the present invention comprises
a branching portion (241) disposed on the first passage (211) between the container (20) and the first valve (231),
a second passage (212) having one end connected to the branching portion (241),
a second depressurizing means (253) connected to the other end of the second passage (212), and
a third valve (233) disposed on the second passage (212), and
the liquid supplying system comprises
f) a sixth means executing a sixth process of driving the second depressurizing means with the third valve opened before execution of the first process so as to suck the liquid into the second passage portion from the container to the third valve.

Another form of the liquid supplying system according to the present invention comprises a seventh means executing a seventh process of returning to the container (20) the liquid remaining in the second passage portion from the container (20) to the third valve (233) after the fifth process.

Another form of the liquid supplying system according to the present invention comprises a means repeating the second to fifth processes twice or more.

A preferable embodiment of a method for driving a liquid supplying system provides a method for driving a liquid supplying system including
a processing chamber (121) having a space (122) of a predetermined volume,
a first depressurizing means (123) depressurizing the space (122) of the processing chamber (121),
a container (20) containing a liquid,
a measuring chamber (151) measuring the liquid, a first passage (111) connecting the container (20) and the processing chamber (121) through the measuring chamber (151), a first valve (131) disposed on the first passage (111) between the container (20) and the measuring chamber (151), a second valve (132) disposed on the first passage (111) between the measuring chamber (151) and the processing chamber (121), and a control part (90) controlling the first depressurizing means (123), the first valve (131), and the second valve (132), and the method comprises a) a first step of executing a first process of driving the first depressurizing means to depressurize the processing chamber so as to form a negative pressure in the processing chamber with the second valve closed;

b) a second step of executing a second process of opening the second valve with the first valve closed so as to introduce the negative pressure of the processing chamber into the measuring chamber;

c) a third step of executing a third process of closing the second valve with the first valve closed so as to retain the negative pressure introduced into the measuring chamber;

d) a fourth step of executing a fourth process of opening the first valve with the second valve closed so as to suck the liquid from the container into the measuring chamber by using the negative pressure of the measuring chamber;

e) a fifth step of executing a fifth process of opening the second valve with the first valve closed so as to suck the liquid in the measuring chamber into the processing chamber by using a vacuum in the processing chamber.

In another form of the method for driving a liquid supplying system, the liquid supplying system includes a branching portion (141) disposed on the first passage (111) between the container (20) and the first valve (131), a second passage (112) having one end connected to the branching portion (141), a second depressurizing means (153) connected to the other end of the second passage (112), and a temporary storage chamber (154) and a third valve (133) disposed on the second passage (112) in order from the one end toward the other end, and the method comprises f) a sixth step of executing a sixth process of driving the second depressurizing means with the third valve opened before execution of the first process so as to suck the liquid into the second passage portion from the container to the temporary storage chamber.

Another form of the method for driving a liquid supplying system comprises a seventh step of executing a seventh process of returning to the container (20) the liquid remaining in the second passage portion from the container (20) to the third valve (133) after the fifth process.

In another form of the method for driving a liquid supplying system the liquid supplying system includes a branching portion (241) disposed on the first passage (211) between the container (20) and the first valve (231), a second passage (212) having one end connected to the branching portion (241), a second depressurizing means (253) connected to the other end of the second passage (212), and a third valve (233) on the second passage (212), and the method comprises f) a sixth step of executing a sixth process of driving the second depressurizing means with the third valve opened before execution of the first process so as to suck the liquid into the second passage portion from the container to the third valve.

Another form of the method for driving a liquid supplying system comprises a seventh step of executing a seventh process of returning to the container (20) the liquid remaining in the second passage portion from the container (20) to the third valve (233) after the fifth process.

In another form of the method for driving a liquid supplying system, the second to fifth processes are repeated twice or more.

Effect of the Invention

According to the liquid supplying system and the method for driving the same configured as described above, a liquid such as a sterilant can accurately be measure.

MODES FOR CARRYING OUT THE INVENTION

Description will hereinafter be made of an example of application of a liquid supplying system according to the present invention to a gas sterilization apparatus. As is well known, the gas sterilization apparatus sterilizes medical devices etc. with a sterilant such as peracetic acid; however, the application of the liquid supplying system of the present invention is not limited to the gas sterilization apparatus.

1. General Structure

Figure 13:
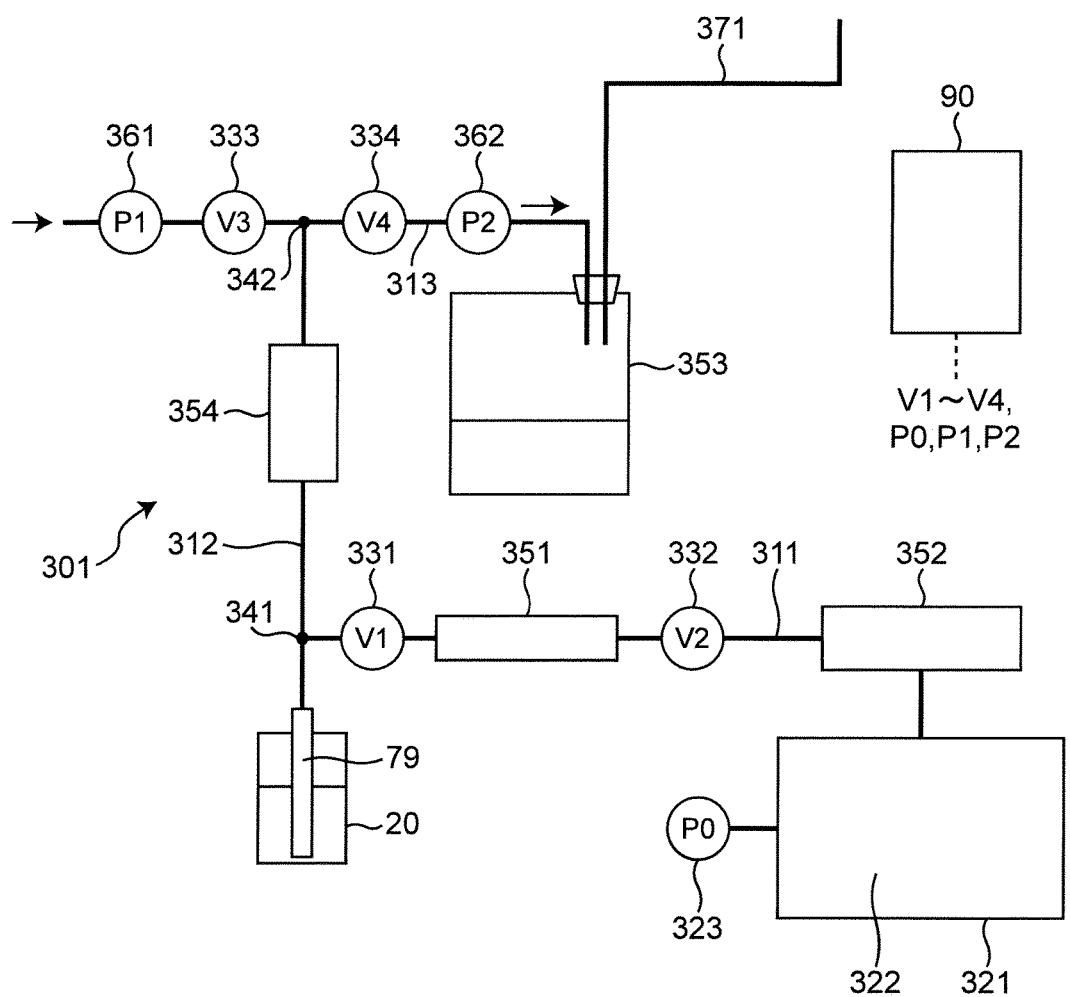
FIG. 13 is a block diagram of a structure of a measuring unit of a third embodiment incorporated in the liquid supplying system according to the present invention.

A liquid supplying system (generally denoted by reference numeral 1) described below roughly includes a supplying unit (generally designated by reference numeral 2) shown in FIGS. 1 to 3 and a measuring unit (101, 201, 301, or 401) shown in FIG. 9, 13, or 15.

2. Supplying Unit

A structure of the supplying unit 2 will be described.

2.1: Housing

The supplying unit 2 has a housing 10 that houses various components described later. For simplicity, the drawings show only a portion of the housing 10, for example, only a portion of a front wall 11 to which an operator faces during operation.

Figure 1:
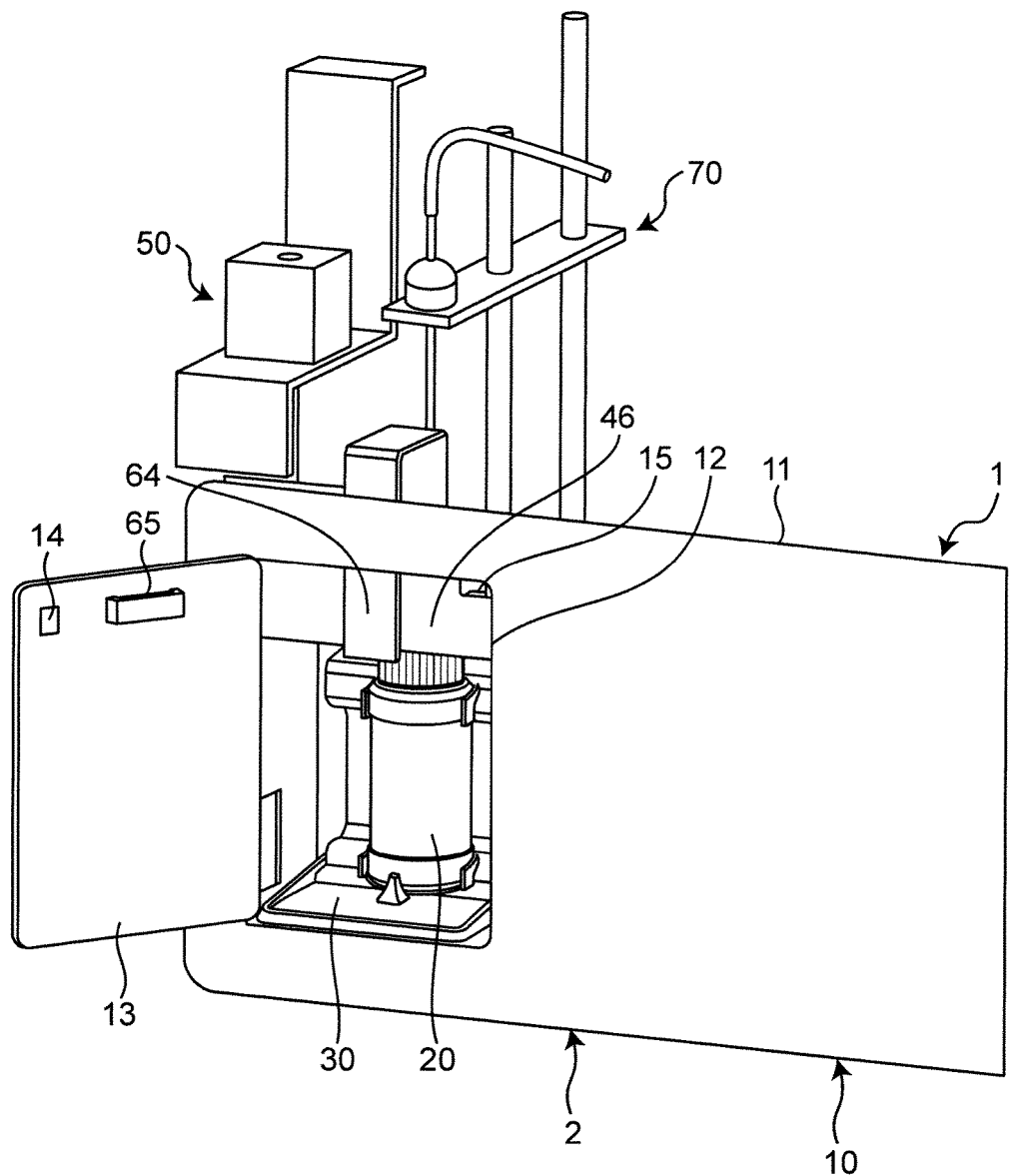
FIG. 1 is a partial perspective view of a liquid supplying system and a supplying unit incorporated therein according to the present invention.

Referring to FIG. 1, the housing front wall 11 has an opening 12 formed in a predetermined place in the housing 10 for inserting a liquid container (hereinafter simply referred to as "container") 20 described later. The opening 12 is preferably configured to be closed by a door 13 having a shape and a size adapted thereto. The type of the door is not limited and may be of any type (e.g., a single opening type, a double opening type, or a sliding type).

The door 13 of the embodiment is a single opening door having a shape (e.g., a substantially quadrangular shape) corresponding to the shape of the opening 12 and has a left end rotatably hinged (not shown) at a corresponding position of the housing 10 when viewed from the front side. A latch mechanism holding the door 13 at a closed position (not shown) is preferably disposed. The latch mechanism may have, for example, a magnetic metal piece 14 attached to an inner surface of the door 13 and a magnet 15 attached to the housing 10 so that the magnet 15 keeps the metal piece 14 in the closed state of the door 13.

2.2: Container

Figure 5:
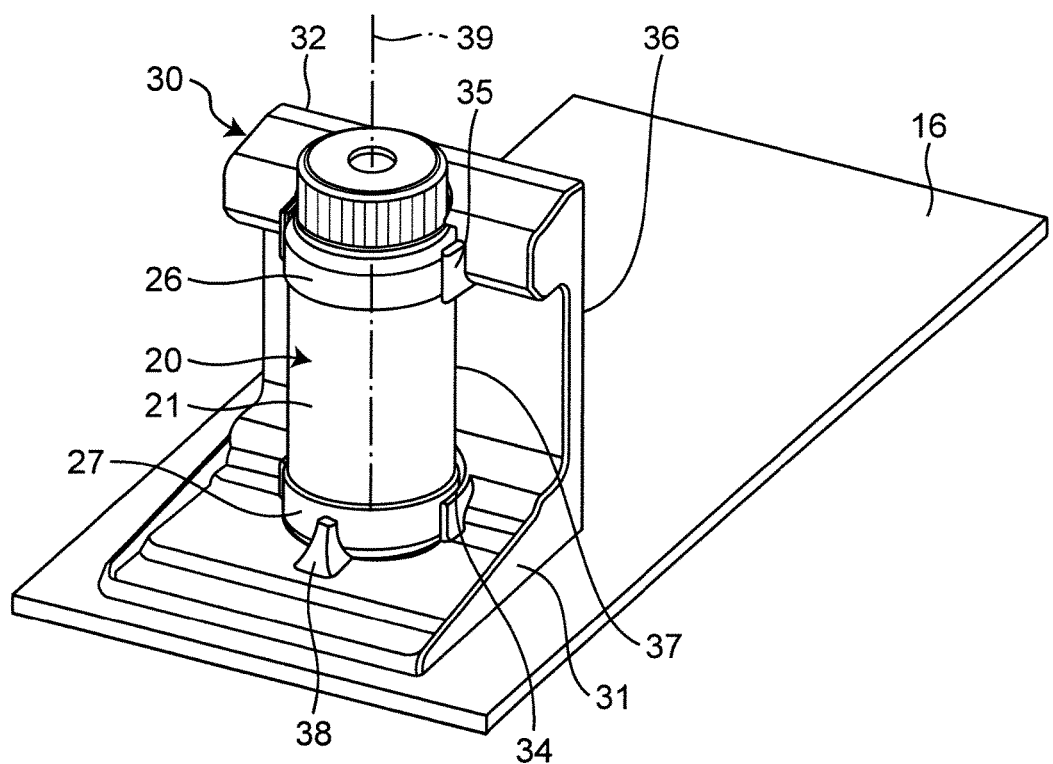
FIG. 5 is a perspective view of a container and a container receiving part of the supplying unit shown in FIGS. 1 to 4.
Figure 6:
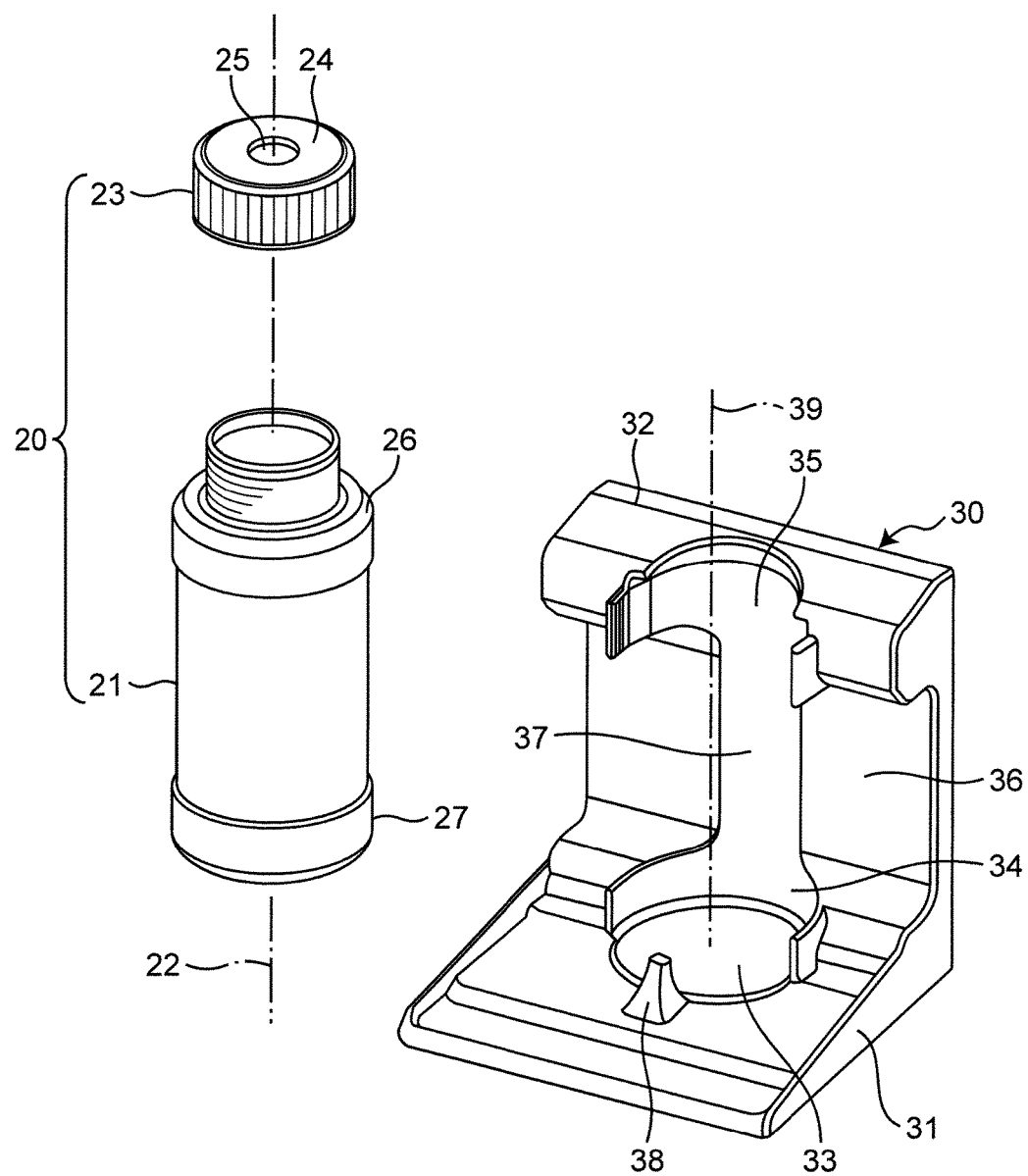
FIG. 6 is an exploded perspective view of the container and the container receiving part of the supplying unit shown in FIGS. 1 to 4.

As shown in FIGS. 5 and 6, the container 20 has a main body 21 containing a chemical liquid (e.g., peracetic acid for sterilization). In the embodiment, the main body 21 is a cylindrical body around a central axis 22 extending in the up-down direction and has a mouth portion in an upper portion. In the embodiment, an external thread (not shown) is integrally formed around the mouth portion of the main body 21, and a lid 23 is attached to the external thread. A central region 25 of a lid ceiling wall 24 is preferably designed thinner than the other portions so that a hollow piercing needle (described later) breaks through the central region 25 with a smaller force as described later.

In the present invention, the main body 21 of the container 20 is made of plastic, glass, or metal. The lid 23 is made of plastic or metal.

The container 20 may not be made up of two members, i.e., the main body and the lid, and may be made up of a single member. Specifically, the container may have a main body integrally formed of a single material and may be filled with a liquid through a sealable mouth portion formed in a portion of the main body.

2.3: Container Receiving Part

As shown in FIGS. 5 and 6, a base 16 forming a portion of a bottom portion of the housing 10 is disposed behind the opening 12. A substantially L-shaped container receiving part 30 is fixed onto the base 16, facing the opening 12. As shown in FIG. 6, the container receiving part 30 has a lower support portion 31 supporting a bottom portion 27 of the container main body 21 and an upper support portion 32 supporting a shoulder portion 26 of the container main body 21. As shown in the figures, the lower support portion 31 has a table 33 made up of a circular raised portion having a size and a shape corresponding to the shape of the main-body bottom portion 27, and a lower half-cylindrical wall 34 having a substantially half-cylindrical recess corresponding to the shape of the main-body lower portion. The upper support portion 32 has an upper half-cylindrical wall 35 having a substantially half-cylindrical recess corresponding to the shape of the main-body shoulder portion 26. In the embodiment, a vertical portion 36 coupling the lower support portion 31 and the upper support portion 32 is provided with a cylindrical wall 37 having a recess of the cylindrical shape of the container main body 21. In the embodiment, a projection 38 is also formed on the lower support portion 31 on the opening side of the table 33.

According to such a structure of this embodiment, the container 20 inserted from the opening 12 is fixed, from a tilted state with the main-body bottom portion 27 engaged with the inside (table side) of the projection 38, by pushing the main-body shoulder portion 26 into the upper half-cylindrical wall 35 and pushing the main-body bottom portion 27 into the lower half-cylindrical wall 34 while raising the container 20. As shown in FIG. 5, in this state, the container 20 has the main-body bottom portion 27 restricted by the table 33, the lower half-cylindrical wall 34, and the projection 38 and the main-body shoulder portion 26 restricted by the upper half-cylindrical wall 35 and is therefore limited in movement (horizontal movement, vertical movement) in all directions, i.e., front-back, left-right, and up-down directions, in an upright state with the central axis 22 of the container 20 made coincident with a vertical axis 39 passing through the center of the table 33.

2.4: Container Housing Chamber

Figure 2:
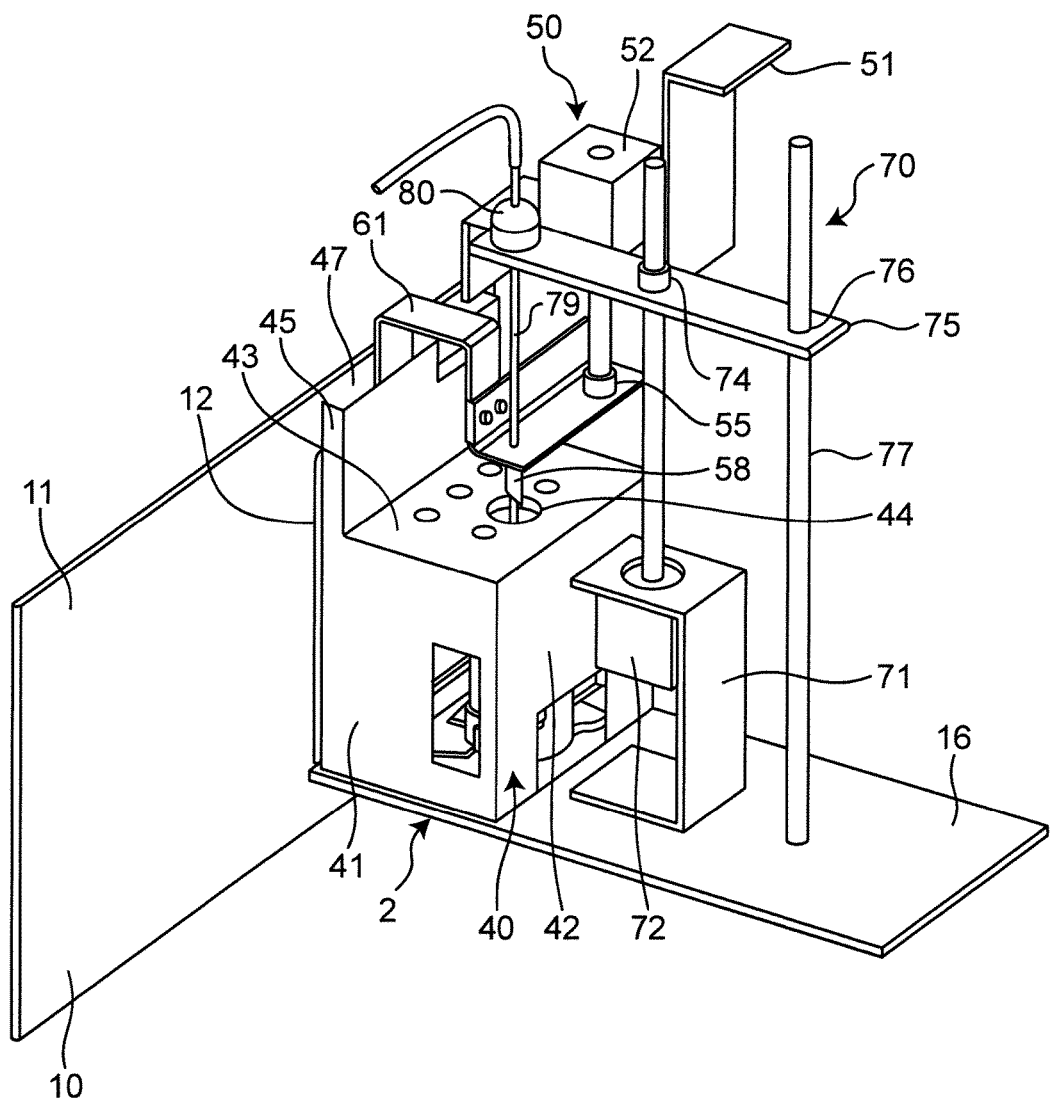
FIG. 2 is a partial perspective view of the liquid supplying system and the supplying unit incorporated therein according to the present invention.
Figure 3:
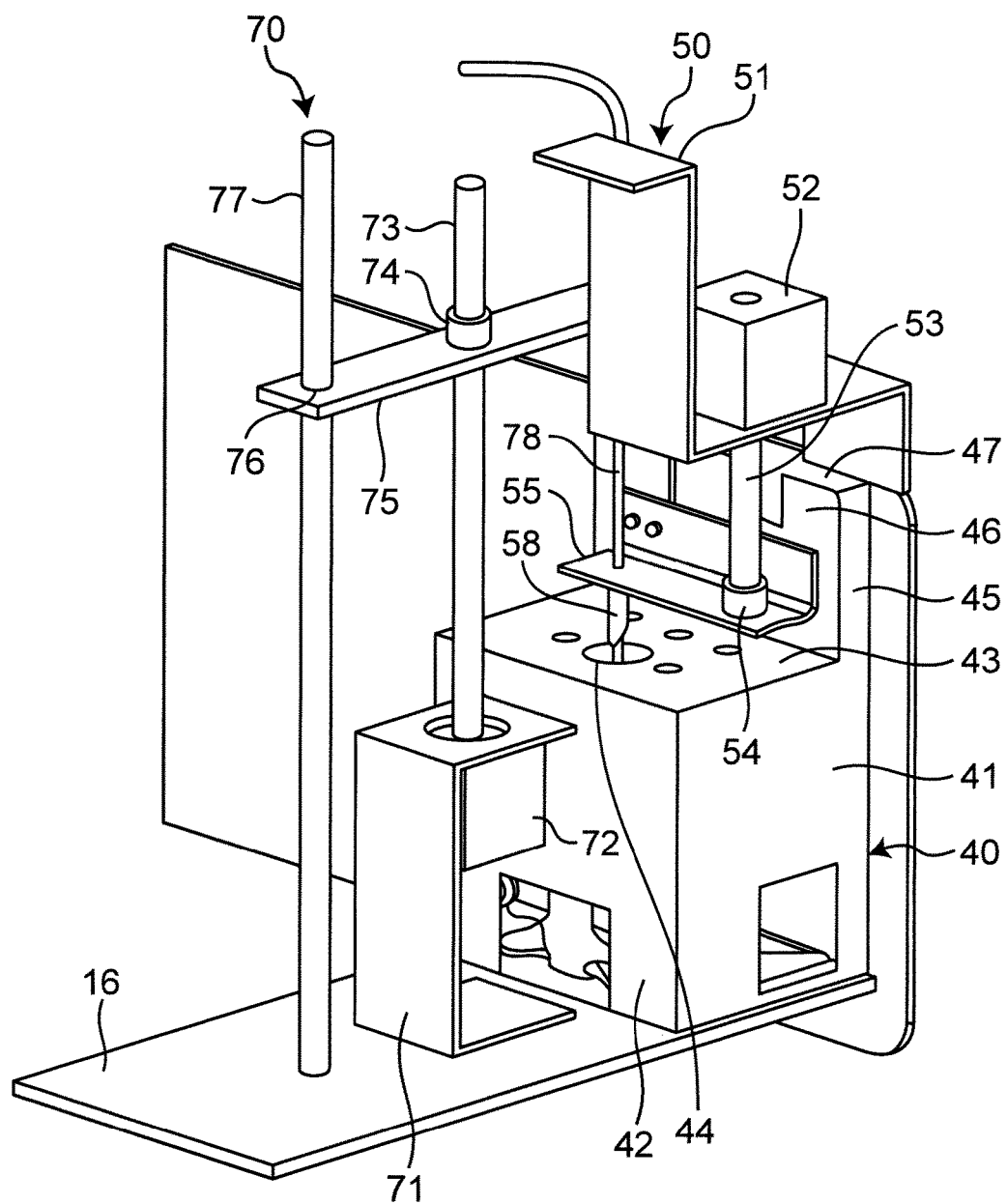
FIG. 3 is a partial perspective view of the liquid supplying system and the supplying unit incorporated therein according to the present invention.
Figure 4:
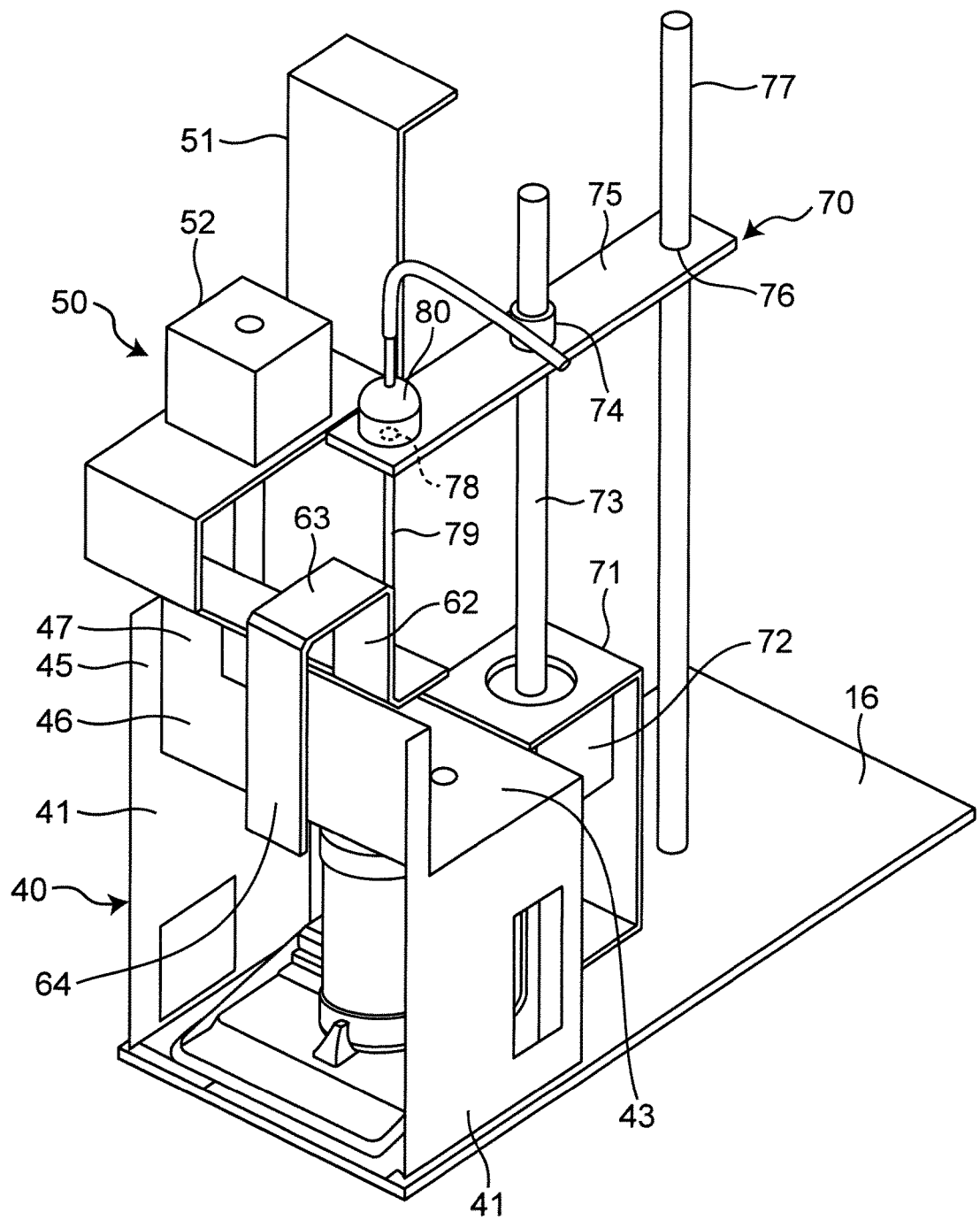
FIG. 4 is a partial perspective view of the liquid supplying system and the supplying unit incorporated therein according to the present invention.

As shown in FIGS. 2 to 4, in the embodiment, a chamber surrounding the container receiving part 30 and the container 20 mounted thereon is formed as a container receiving chamber 40 inside the opening 12. The container housing chamber 40 is made up of left/right side walls 41, a back wall 42 on the rear side, and a ceiling wall 43 and is openable to the outside through the opening 12. A circular window 44 around the vertical axis 39 is formed in the ceiling wall 43 so that a hollow piercing needle described later can access the container 20 through this window 44.

Portions of the left/right side walls 41 adjacent to the housing front wall 11 is extended upward to form extended side walls 45. An extended back wall 46 extending in the left-right direction is formed away from the housing front wall 11 between rear vertical edges of the left/right extended side walls 45, and a front end of the ceiling wall 43 is coincident with a lower end of this extended back wall 46 so that a gap 47 is formed between the extended side walls 45, the extended back wall 46, and the housing front wall 11.

As shown in FIG. 1, a portion (lower portion) of the extended back wall 46 is exposed in the opening 12. A portion (an engaged part 65) of a door lock mechanism 60 described later is disposed on an upper portion of the inner surface of the door 13 facing an opening exposed surface of the extended back wall 46.

2.5: Needle, First Moving Mechanism, Lock Mechanism

As shown in FIGS. 2 to 4, a fixed bracket (first fixed part) 51 is disposed behind the housing front wall 11. The fixed bracket 51 is fixed to the housing 10 indirectly via an appropriate member or directly without via such a member. The fixed bracket 51 supports a driving part (first driving part) 52. The driving part 52 has an electric motor. A ball screw 53 oriented in the vertical direction is coupled to a rotating shaft of the motor so that the ball screw 53 rotates according to forward and reverse rotation of the motor. The ball screw 53 is coupled to a movable bracket (first movable part) 55 via a nut 54 so that the movable bracket 55 moves up and down according to the rotation of the ball screw 53.

The movable bracket 55 is preferably provided with an appropriate rotation preventing means so that the movable bracket 55 moves in the up-down direction without rotating (corotating) together with the rotation of the ball screw 53. For example, a vertical guide 56 (see FIG. 7) extending in parallel with the ball screw 53 is fixed to the housing 10 or the base 16, and the movable bracket 55 or a lock plate 61 (described later) coupled thereto is restricted such that movement is made only in the up-down direction along the vertical guide 56.

The movable bracket 55 also has a hole 57 (see FIG. 7) formed on the vertical axis 39 of the container housing chamber 40 to penetrate the movable bracket 55 in the up-down direction. A hollow piercing needle 58 is fixed to a lower surface of the movable bracket 55 adjacent to the hole 57, and a central axis of a lumen of the hollow piercing needle 58 and the central axis of the hole 57 are aligned on the vertical axis 39 (see FIG. 6).

As the name implies, the hollow piercing needle 58 has a hollow cylindrical body obliquely cut at a lower portion to form a steeple portion 59. Although the material of the hollow drilling needle 58 is not limited, if the liquid is strongly acidic or strongly alkaline, the needle is made of a material not corroded due to contact with the liquid or has a surface coated with such a material. A typical corrosion-resistance material is polytetrafluoroethylene.

Figure 7:
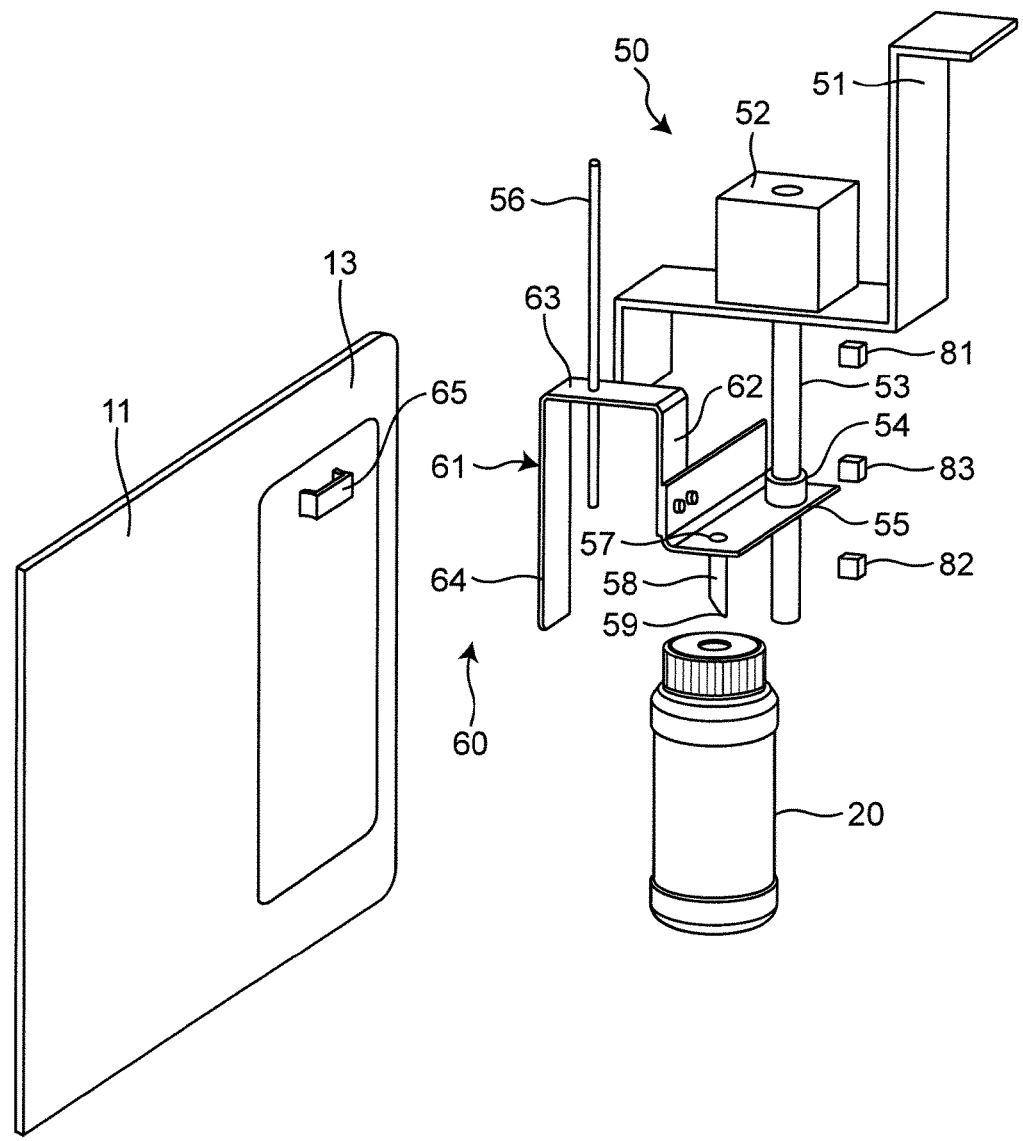
FIG. 7 is a perspective view of a first moving mechanism of the supplying unit shown in FIGS. 1 to 4.
Figure 8:
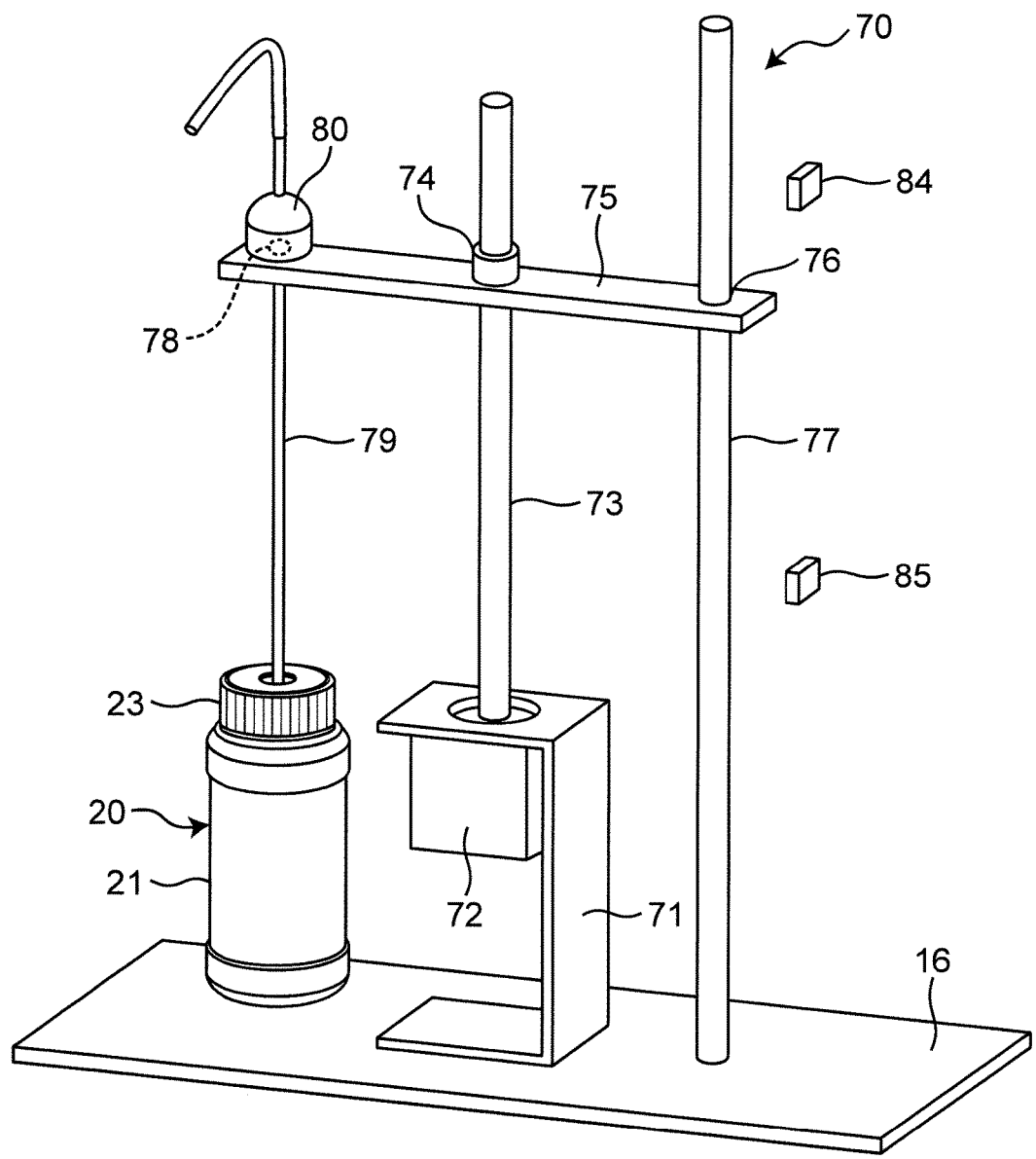
FIG. 8 is a perspective view of a second moving mechanism of the supplying unit shown in FIGS. 1 to 4.

As shown in FIG. 7, the movable bracket 55 has the lock plate 61 functioning as a portion of a mechanism locking the door 13. In the embodiment, the lock plate 61 is formed by bending an elongated plate into a bracket shape and includes a first portion 62 extending vertically upward from the movable bracket 55, a second portion 63 extending horizontally forward from an upper end of the first portion 62 toward the front wall 11, and a third portion 64 extending vertically downward from an end of the second portion 63. The third portion (hereinafter referred to as "engaging part") 64 enters the gap 47 formed between the front wall 11 and the extended back wall 46 from above. Corresponding to the engaging part 64, the engaged part 65 engageable with the engaging part 64 is disposed in a region of the door inner surface facing the extended back wall 46, and the lock mechanism 60 is made up of the engaged part 64 and the engaged part 65. In the embodiment, the engaging part 64 is an elongated plate extending in the vertical direction, and the engaged part 65 is formed of a frame allowing entry of the plate.

As described above, the fixed bracket 51, the driving portion 52, the ball screw 53, the nut 54, and the movable bracket 55 constitute a first moving mechanism 50 moving the hollow piercing needle 58 between an elevated position (first needle position) at which the hollow piercing needle 58 is sufficiently retreated above the container 20 and a lowered position (second needle position) at which the hollow piercing needle 58 breaks and penetrates through the lid 23 of the container 20.

The first moving mechanism 50 and the lock mechanism 60 are designed such that when the hollow piercing needle 58 is at the first needle position, the door 13 is openable (unlocked) without engagement of the engaging part 64 with the engaged part 65, that when the hollow piercing needle 58 is at a position somewhat lowered from the first needle position (however, the hollow piercing needle 58 is separated by a sufficient distance from the lid 23 of the container 20; this position will hereinafter be referred to as a "third needle position"), the engaging part 64 is engaged with the engaged part 65, and that while the hollow piercing needle 58 moves further downward from the third needle position to the second needle position, the engaging part 64 is constantly engaged with the engaged part 65 to keep the door 13 unopenable (locked).

To determine whether the hollow piercing needle 58 is located at the first needle position, the second needle position, or the third needle position, detectors 81, 82, 83 are preferably disposed for detecting the position of the movable bracket 55 supporting the hollow piercing needle 58.

2.6: Second Moving Mechanism

As shown in FIGS. 2 to 4, a fixed bracket 71 is fixed onto the base 16. The fixed bracket 71 supports a driving part (second driving part) 72. The driving part 72 has an electric motor. A ball screw 73 oriented in the vertical direction is coupled to a rotating shaft of the motor so that the ball screw 73 rotates in accordance with forward and reverse rotation of the motor. The ball screw 73 is coupled to a movable bracket (second movable part) 75 via a nut 74.

The movable bracket 75 has a through-hole 76. The base 16 supports a guide rod 77 extending in parallel with the ball screw 73, and the guide rod 77 penetrates the through-hole 76 of the movable bracket 75. Therefore, when the ball screw 73 rotates, the movable bracket 75 moves up and down while being guided by the guide rod 77.

The movable bracket 75 has a through-hole 78 on an extension of the vertical axis 39. A hollow suction tube 79 made of a rigid material is inserted through the through-hole 78 movably in the up-down direction along the vertical axis 39. To position the suction tube 79 relative to the movable bracket 75, a holder 80 is fixed to the movable bracket 75. The holder 80 is made of an elastic material such as rubber, for example, and is provided with a small vertical hole having a diameter smaller than the outer diameter of the moveable bracket 75, and the suction tube 79 is fitted into the vertical hole. Therefore, the suction tube 79 can be moved up and down relative to the movable bracket 75 and can be fixed to the suction tube 79 with a lower end of the suction tube 79 set to a desired height.

In the embodiment, the length of the suction tube 79 extending downwardly from the movable bracket 75 is adjusted such that when the hollow piercing needle 58 is at the first needle position (elevated position), the suction tube 79 is at least partially located in the lumen of the hollow piercing needle 58 and holds the hollow piercing needle 58 on the vertical axis 39 and that when the hollow piercing needle 58 is at the second needle position (lowered position), the suction tube 79 enters the inside of the container 20 with a lower end thereof coming into slight contact or substantially no contact with an inner bottom surface of the container 20.

As described above, the fixed bracket 71, the driving portion 72, the ball screw 73, the nut 74, and the movable bracket 75 constitute a second moving mechanism 70 moving the suction tube 79 between an elevated position (first tube position) at which the suction tube 79 is sufficiently retreated above the container 20 and a lowered position (second tube position) at which the suction tube 79 penetrates the lid 23 of the container 20 with the lower end thereof located in the vicinity of the container bottom surface.

To determine whether the suction tube 79 is located at the first tube position or the second tube position, detectors 84, 85 are preferably disposed for detecting the position of the movable bracket 75.

2.7: Operation

An operation of the supplying unit 2 will be described.

2.7.1: Mounting of Container

While the container 20 is not mounted on the container housing chamber 40, the hollow piercing needle 58 is at the first needle position, and the suction tube 79 is at the first tube position, so that the hollow piercing needle 58 and the aspiration tube 79 are retreated above the container housing chamber 40. Therefore, the engaging part 64 of the lock mechanism 60 is away from the engaged part 65, and the door 13 is in an openable state (unlocked state).

When mounting the container 20 in the container housing chamber 40, the door 13 is opened, and the container 20 is placed in the container housing chamber 40 through the opening 12. At this step, the container 20 is kept tilted and inserted from the main-body bottom portion 27 into the container storage chamber 40, and the main-body bottom portion 27 is positioned inside the projection 38 of the container receiving part 30. While the posture of the container 20 is changed from the tilted state to the upright state, the container bottom portion 27 is pushed into the lower half-cylindrical wall 34, and the main-body shoulder portion 26 is pushed into the upper half-cylindrical wall 35. As a result, the container 20 is stably held in the container receiving part 30. Subsequently, the door 13 is closed.

2.7.2: Lid Opening Process

In the case of supplying a liquid from the container 20 fixed to the container housing chamber 40, for example, an operator presses a lid opening process start switch (not shown) disposed on the housing 10, and a computer 90 incorporated in a control part of a system 1 starts a program stored therein and executes a lid opening process described below.

When starting the lid opening process, the computer 90 drives the driving part 52 to lower the hollow piercing needle 58 from the first needle position to the second needle position. During the lowering, when the hollow piercing needle 58 reaches the third needle position, the engaging part 64 of the lock mechanism 60 engages with the engaged part 65 to put the door 13 into the unopenable state (locked state).

After passing through the third needle position, the hollow piercing needle 58 goes through the window 44 of the ceiling wall 43 of the container housing chamber 40 and breaks and penetrates through the central region 25 of the lid 23. The computer 90 stops the driving part 52 with the hollow piercing needle 58 penetrating the lid 23 and maintains this state (the second needle position). The computer 90 preferably also drives the drive 72 in conjunction with the lowering of the hollow drilling needle 58 to maintain a state in which at least a portion of the suction tube 79 is constantly located in the lumen of the hollow drilling needle 58 during the lowering of the hollow drilling needle 58. However, a distance between the suction tube 79 and the lid 23 is maintained so as not to bring the lower end of the suction tube 79 into contact with the lid 23 until the hollow piercing needle 58 penetrates the lid 23.

After the lid is opened, the hollow piercing needle 58 may be maintained at the position (second needle position) of penetration through the lid 23. Alternatively, after opening the lid, the computer 90 may elevate and separate the hollow drilling needle 58 from the lid 23. Subsequently, when sucking the liquid, the computer 90 drives the driving part 72 to insert the lower end of the suction tube 79 into the liquid. The suction tube 79 may constantly be immersed in the liquid regardless of whether the liquid is sucked or not sucked or may be maintained above a liquid level when the liquid is not sucked.

2.7.3: Container Replacement

When replacing the container, an operator presses a switch (not shown) dispose on the housing 10. This causes the computer 90 of the system 1 to drive the driving parts 52, 72 to return the hollow piercing needle 58 to the first needle position and return the suction tube 79 to the first tube position. As a result, the lock mechanism 60 is released. Subsequently, the operator can open the door 13 and take out the container 20 from the container storage chamber 40. A procedure of taking out the container 20 is opposite to the procedure of mounting. The container may be replaced also when it is detected that a remaining amount of the liquid in the container 20 becomes equal to or less than a predetermined amount or when it is detected that the expiration date of the container 20 or the liquid is reached. When the container replacement switch is pressed or when it is detected that the remaining amount of the liquid becomes equal to or less than a predetermined amount, the liquid remaining in the container 20 is sucked and collected into a waste liquid storage chamber (e.g., denoted by reference numeral 153 in FIG. 9) (this process is referred to as a "container replacement preparation process").

3. Measuring Unit

An embodiment of a measuring unit will be described.

3.1: First Embodiment

A measuring unit 101 of a first embodiment will be described.

3.1.1: Structure

Figure 9:
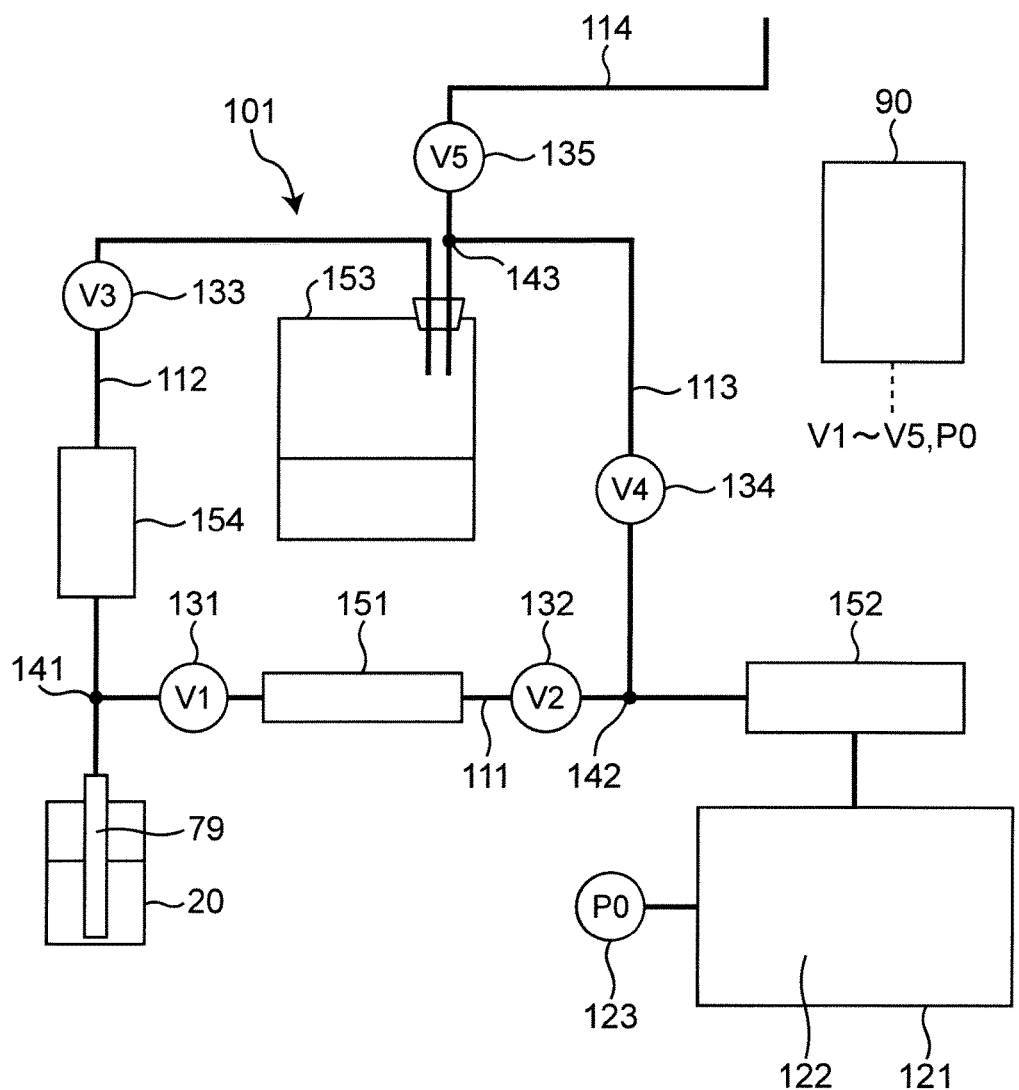
FIG. 9 is a block diagram of a structure of a measuring unit of a first embodiment incorporated in the liquid supplying system according to the present invention.

As shown in FIG. 9, the measuring unit 101 has a first transport passage 111, a second transport passage 112, a third transport passage 113, and a fourth transport passage 114 for transporting a liquid. The first transport passage 111 has one end connected to the upper end of the suction tube 79 and the other end is connected to a processing chamber (first chamber) 121. The processing chamber 121 is, for example, a sterilization chamber of a gas sterilization apparatus and is connected to a vacuum pump (first depressurizing means) 123 so that a space 122 in the processing chamber 121 can be depressurized to form a vacuum. Although not shown, the processing chamber 121 is provided with various instruments (e.g., a pressure detector, a temperature detector) necessary for properly managing a sterilization process.

The first transport passage 111 is provided with a first valve 131, a measuring chamber (second chamber) 151, a second valve 132, and a vaporizing chamber 152 in order from the suction tube 79 toward the processing chamber 121. A volume (second volume) of the measuring chamber 151 is smaller than a volume (first volume) of the processing chamber 12 and, for example, when the volume of the processing chamber 121 is 100 to 150 liters, the volume of the measuring chamber 151 is set to 2 to 7 milliliters. The first transport passage 111 has a first branching portion 141 between the first valve and the suction tube 79 and a second branching portion 142 between the second valve 132 and the vaporizing chamber 152. The second transport passage 112 has one end connected to the first branching portion 141 and the other end connected to the waste liquid storage chamber 153 and is provided with a temporary storage chamber 154 and a third valve 133 in order from the first branching portion 141 toward the waste liquid storage chamber 153. The third transport passage 113 has one end connected to the second branching portion 142 and the other end connected to the waste liquid storage chamber 153 and is provided with a fourth valve 134 and a third branching portion 143 in order from the second branching portion 142 toward the waste liquid storage chamber 153. The fourth transport passage 114 has a fifth valve 135 and has one end connected to the third branching portion 143 and the other end opened to the atmosphere.

For each of the first to fifth valves 131 to 135 described above, an electromagnetic valve is suitably used. The vacuum pump 123 and the first to fifth valves 131 to 135 are connected to the computer 90 and are configured to operate based on an output of the computer 90.

3.1.2: Operation

Figure 10:
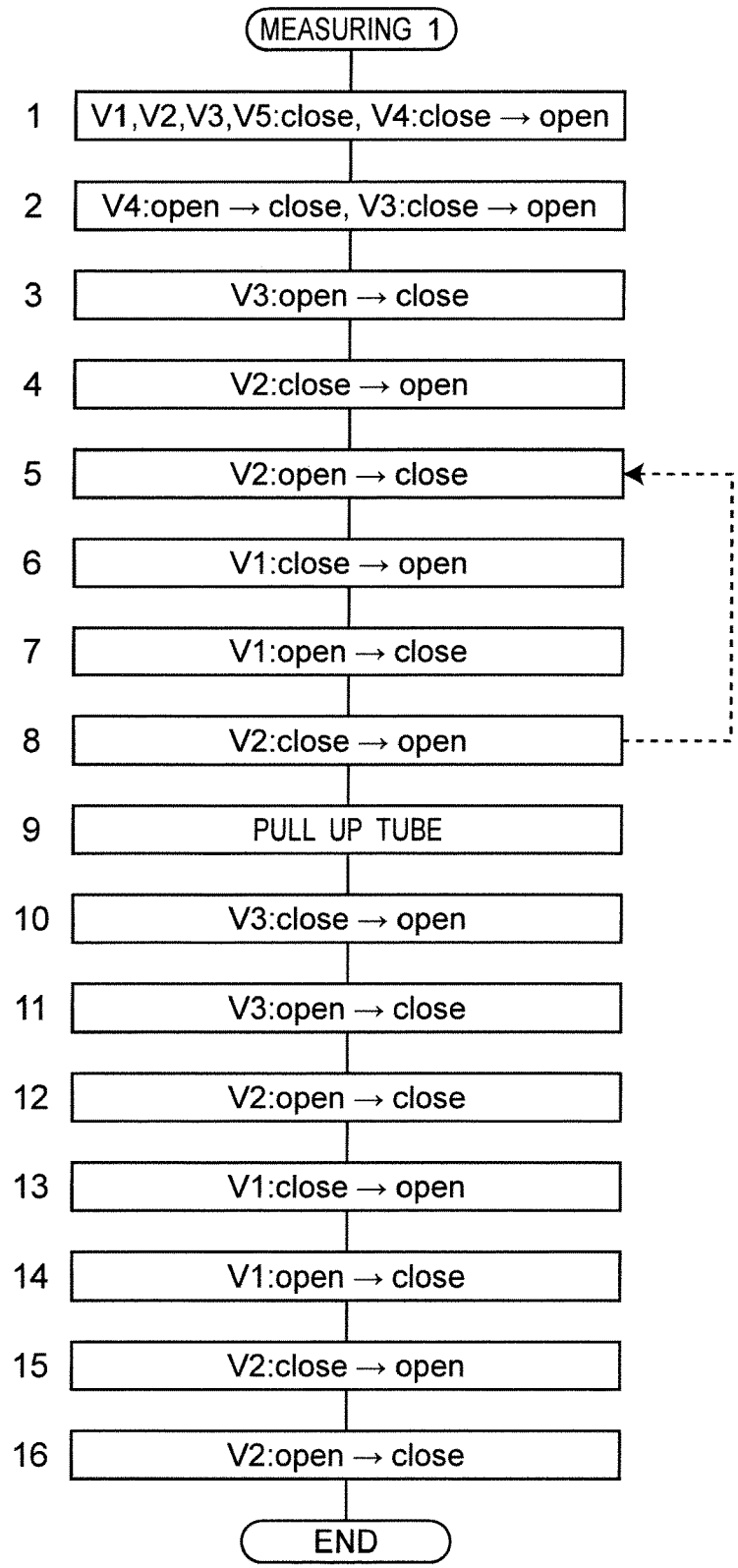
FIG. 10 is a flowchart of an operation of the measuring unit shown in FIG. 9.

An operation of the measuring unit 101 will be described with reference to FIG. 10.
(Step 1)
When detecting that a tip of the suction tube 79 inserted into the container 20 has reached the container bottom surface or the vicinity thereof, the computer 90 closes the first, second, third, and fifth valves 131, 132, 133, 135 and opens the fourth valve 134. The computer 90 also drives the vacuum pump 123. As a result, the processing chamber 121, the vaporizing chamber 152, and the waste liquid storage chamber 153 are set at a predetermined vacuum pressure. The vacuum pressure of the waste liquid storage chamber 153 is used for the container replacement preparation process described above. The same applies to the other embodiments described later.

The valve 134 may be opened not only in the case described above but also, for example, when the vacuum pump 123 is driven and the pressure in the processing chamber 121 reaches 80,000 Pa, for example. The same applies to the other embodiments described below.

The tip of the suction tube 79 having reached the container bottom surface or the vicinity thereof can be detected based on signals from the detectors 81, 82, 83. Alternatively, the position of the suction tube 79 can be detected based on the driving time of the driving part 72.
(Step 2)
After a lapse of a predetermined time, the computer 90 closes the fourth valve 134 and opens the third valve 133. As a result, the liquid in the container 20 is sucked through the suction tube 79 and supplied to the temporary storage chamber 154. In this way, in this embodiment, the third valve 133, the fourth valve 134, the fifth valve 135, and the waste liquid storage chamber 153 function as a depressurizing means (second depressurizing means) depressurizing the temporary storage chamber 154 to form a vacuum.
(Step 3)
After a lapse of a predetermined time, the computer 90 closes the third valve 133. The time from opening to closing the third valve 133 is set such that a predetermined amount of the liquid is filled into the temporary storage chamber 154. As a result, the first transport passage portion from the suction tube 79 to the temporary storage chamber 154 is filled with the liquid
(Step 4)
The computer 90 opens the second valve 132 to allow the measuring chamber 151 to communicate with the vaporizing chamber 152 and the processing chamber 121 and sucks air in the measuring chamber 151.
(Step 5)
After a lapse of a predetermined time, the computer 90 closes the second valve 132. As a result, the measuring chamber 151 is set to a predetermined vacuum pressure.
(Step 6)
The computer 90 opens the first valve 131. As a result, the liquid in the container 20 is sucked into the measuring chamber 151. As described above, since the suction tube 79 and the subsequent first transport passage portion to the temporary storage chamber 154 are filled with the liquid, no air enters the measuring chamber 151, and the predetermined amount of the liquid is reliably filled into the measuring chamber 151.
(Step 7)
The computer 90 closes the first valve 131 after a predetermined time. This time is set to the time required for completely or substantially completely filing the measuring chamber 151 with the liquid.
(Step 8)
The computer 90 opens the second valve 132. As a result, the liquid in the measuring chamber 151 is drawn by the vacuum of the processing chamber 121 and the vaporizing chamber 152 and vaporized into a gas in the vaporizing chamber 152, and the gas is supplied to the processing chamber 121. Through the steps described above, the predetermined amount (corresponding to the volume of the measuring chamber) of the liquid is gasified, supplied to the processing chamber 121, and utilized for the sterilization process in the chamber.

The amount of the liquid supplied to the processing chamber 121 can be adjusted by repeating steps 5 to 7 described above after step 8. The number of times of repetition varies depending on the volume of the measuring chamber 151.
(Step 9)
When the predetermined amount of the liquid is supplied through the process described above, the computer 90 drives the driving part to pull up the suction tube 79 from the liquid and keeps the suction tube 79 out of contact with the liquid.
(Step 10)
The computer 90 opens the third valve 133 and recovers the liquid remaining in the temporary storage chamber 154 and the second transport passage 112 and the suction tube 79 communicating therewith to the waste liquid storage chamber 153 kept in a vacuum.
(Step 11)
After a lapse of a predetermined time, the computer 90 closes the third valve 133 and terminates the recovery of the remaining liquid.
(Step 12)
The computer 90 closes the second valve 132.
(Step 13)
The computer 90 opens the first valve 131 and sucks the liquid remaining on the downstream side of the first valve 131 into the vaporizing chamber 152.
(Step 14)
After a lapse of a predetermined time, the computer 90 closes the first valve 131.
(Step 15)
The computer 90 opens the second valve 132. As a result, the liquid in the measuring chamber 151 is supplied to the processing chamber 121.
(Step 16)
The computer 90 closes the second valve 132 after a predetermined time. This time is set to the time required for completely sucking the liquid or gas remaining in the vaporizing chamber 152 etc. into the processing chamber 121.

As described above, according to the measuring unit 101 of the first embodiment, the predetermined amount of the liquid is accurately measured, vaporized, and supplied to the processing chamber 121 (e.g., the gas sterilization chamber).

3.2: Second Embodiment

The measuring unit 201 of a second embodiment will be described.

3.2.1: Structure

Figure 11:
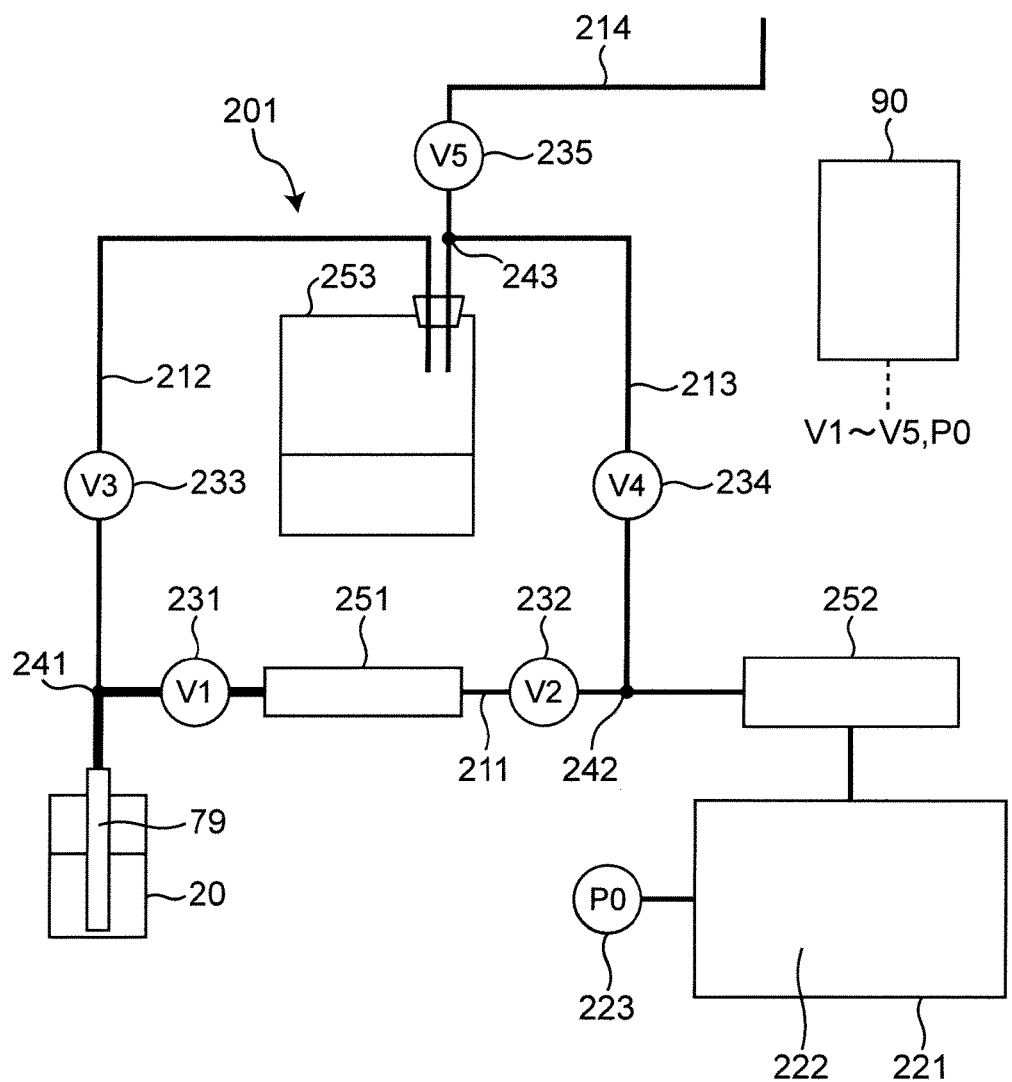
FIG. 11 is a block diagram of a structure of a measuring unit of a second embodiment incorporated in the liquid supplying system according to the present invention.

As shown in FIG. 11, the measuring unit 201 of the second embodiment is different from the measuring unit of the first embodiment in that the unit does not include a temporary storage chamber.

3.2.2: Operation

Figure 12:
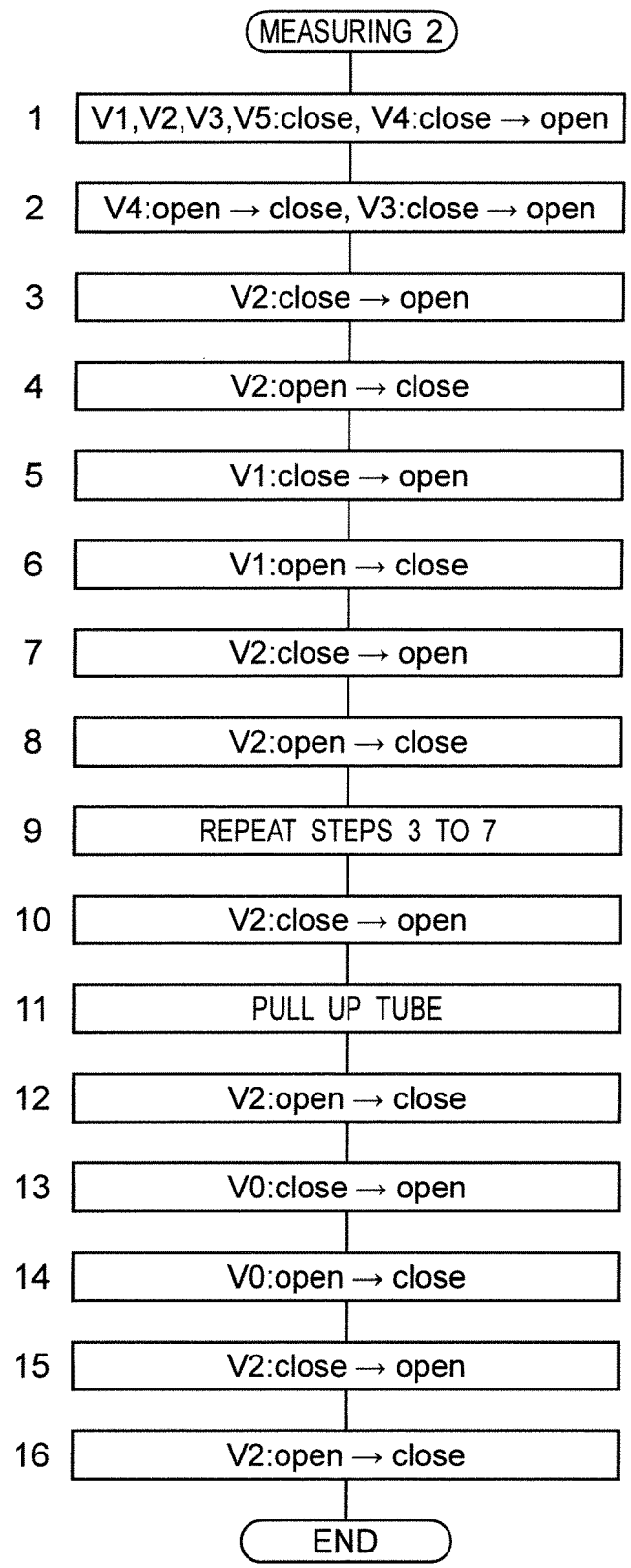
FIG. 12 is a flowchart of an operation of the measuring unit shown in FIG. 11.

An operation of the measuring unit 201 will be described with reference to FIG. 12.
(Step 1)
When detecting that a tip of the suction tube 79 inserted into the container 20 has reached the container bottom surface or the vicinity thereof, the computer 90 closes first, second, third, fifth valves 231, 232, 233, 235 and opens a fourth valve 234. The computer 90 also drives a vacuum pump 223 to set a processing chamber 221, a vaporizing chamber 252, and a waste liquid storage chamber 253 to a predetermined vacuum pressure.

The tip of the suction tube 79 having reached the container bottom surface or the vicinity thereof can be detected based on signals from the detectors 81, 82, 83. Alternatively, the position of the suction tube 79 can be detected based on the driving time of the driving part 72.

(Step 2)
The computer 90 closes the fourth valve 234 and opens the third valve 233. As a result, the liquid in the container 20 is sucked so that the suction tube 79 and a second transport passage portion from the suction tube 79 to the third valve 233 are filled with the liquid. In this way, in this embodiment, the third valve 133, the fourth valve 134, the fifth valve 135, and the waste liquid storage chamber 153 function as a depressurizing means (third depressurizing means) depressurizing the second transport passage portion to form a vacuum.
(Step 3)
The computer 90 opens the second valve 232 to allow a measuring chamber 251 to communicate with the vaporizing chamber 252 and the processing chamber 221 and sucks air in the measuring chamber 251.
(Step 4)
After a lapse of a predetermined time, the computer 90 closes the second valve 232 and sets the measuring chamber 251 to a predetermined vacuum pressure.
(Step 5)
The computer 90 opens the first valve 231. As a result, the liquid in the container 20 is sucked into the measuring chamber 251. In this case, since the suction tube 79 and the second transport passage portion from the suction tube 79 to the third valve 233 are filled with the liquid and no air exists, a predetermined amount of the liquid is sucked into the measuring chamber 251.
(Step 6)
After a lapse of a predetermined time, the computer 90 closes the first valve 231. This time is set to the time required for completely or substantially completely filing the measuring chamber 151 with the liquid.
(Step 7)
The computer 90 opens the second valve 232. As a result, the liquid in the measuring chamber 251 is drawn by the vacuum in the processing chamber 221 and the vaporizing chamber 252 and vaporized into a gas in the vaporizing chamber 252, and the vaporized gas is supplied to the processing chamber 221.
(Step 8)
After a lapse of a predetermined time, the computer 90 closes the second valve 232. This time is set to the time required for completely or substantially completely supplying the liquid in the measuring chamber 251 to the processing chamber 121. Through the steps described above, the predetermined amount (corresponding to the volume of the measuring chamber) of the liquid is gasified, supplied to the processing chamber 221, and utilized for the sterilization process in the chamber.
(Step 9)
The amount of the liquid supplied from the container 20 to the processing chamber 221 by the process described above is limited, and when the total amount of the liquid required for the processing chamber 221 is smaller than one supply amount, steps 3 to 6 described above are repeated after step 8.
(Step 10)
To supply the liquid filled in the measuring chamber 251 at immediately preceding Step 6 to the processing chamber 221, the computer 90 opens the second valve 232 and sends out the liquid in the measuring chamber 251.
(Step 11)
The computer 90 drives the driving part 72 to pull up the suction tube 79 from the liquid and keeps the suction tube 79 out of contact with the liquid.

(Step 12)
The computer 90 closes the second valve 232 after a lapse of a predetermined time.
(Step 13)
The computer 90 opens the first valve 231 and sucks the liquid remaining in the pulled-up suction tube 79 into the measuring chamber 251.
(Step 14)
The computer 90 closes the first valve 231 after a lapse of a predetermined time.
(Step 15)
The computer 90 opens the second valve 232 and supplies the liquid in the measuring chamber 251 from the vaporizing chamber 252 to the processing chamber 221.
(Step 16)
The computer 90 closes the second valve 232 after a lapse of a predetermined time.

As described above, according to the measuring unit 201 of the second embodiment, at steps 11 to 16, the liquid present in the lumen from the first valve 231 to the end of the suction tube 79 is collected in the measuring chamber and supplied to the processing chamber.

3.3: Third Embodiment

The measuring unit 301 of a third embodiment will be described.
3.3.1: Structure As shown in FIG. 13, the measuring unit 301 according to the third embodiment has a first transport passage 311, a second transport passage 312, and a third transport passage 313 for transporting a liquid. The first transport passage 311 has one end connected to the upper end of the suction tube 79 and the other end connected to a processing chamber 321. The processing chamber 321 is, for example, a sterilization chamber of a gas sterilization apparatus and is connected to a vacuum pump 323 so that a space 322 in the processing chamber 321 can be made vacuum. Although not shown, the processing chamber 321 is provided with various instruments (e.g., a pressure detector, a temperature detector) necessary for properly managing the sterilization process.

The first transport passage 311 is provided with a first valve 331, a measuring chamber 351, a second valve 332, and a vaporizing chamber 352 in order from the suction tube 79 toward the processing chamber 321. The first transport passage 311 has a first branching portion 341 between the first valve and the suction tube 79. The second transport passage 312 has one end connected to the first branching portion 341 and the other end connected to a second branching portion 342 and is provided with a temporary storage chamber 354 between the first branching portion 341 and the second branching portion 342. The third transport passage 313 has one end opened to the atmosphere and the other end connected to a waste liquid storage chamber 353 with a first pump 361, a third valve 333, the second branching portion 342, a fourth valve 334, and a second pump 362 arranged between the one end and the other end. The inside of the waste liquid storage chamber 353 is opened to the atmosphere via an exhaust pipe 371.

For each of the first to fourth valves 331 to 334 described above, an electromagnetic valve is suitably used. The vacuum pump 323 and the first to fourth valves 331 to 334 are connected to the computer 90 and are configured to operate based on an output of the computer 90.

3.3.2: Operation

Figure 14:
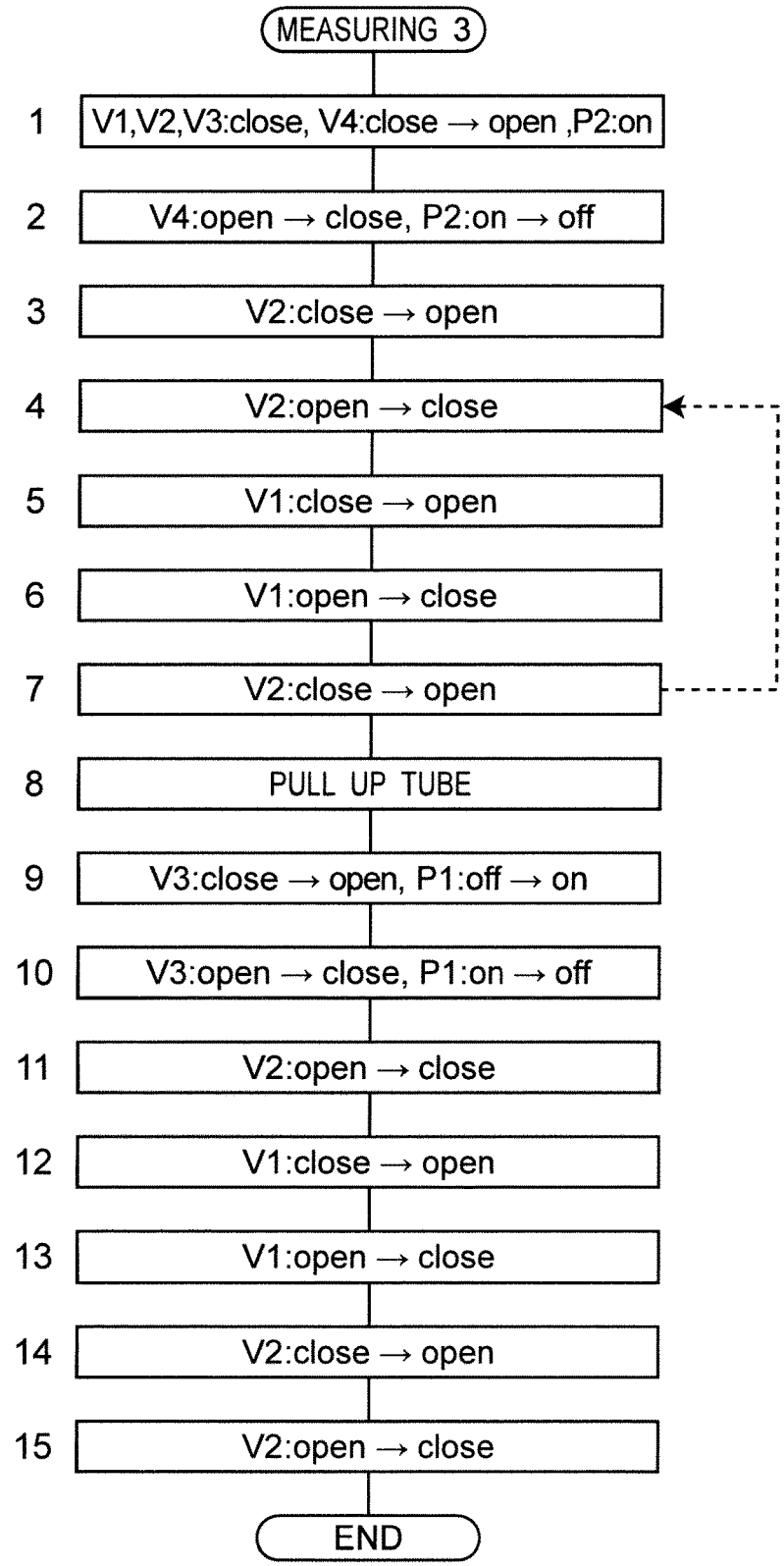
FIG. 14 is a flowchart of an operation of the measuring unit shown in FIG. 13.

An operation of the measuring unit 301 will be described with reference to FIG. 14.

(Step 1)
When detecting that the tip of the suction tube 79 inserted into the container 20 has reached the container bottom surface or the vicinity thereof, the computer 90 closes the first, second, and third valves 331, 332, 333 and opens the fourth valve 334. The computer 90 also drives the second pump 362. As a result, the liquid in the container 20 is sucked through the suction tube 79 and supplied to the temporary storage chamber 354.
(Step 2)
After a lapse of a predetermined time, the computer 90 closes the fourth valve 334 and stops the second pump 362. The predetermined time in this case is set such that a predetermined amount of the liquid is filled into the temporary storage chamber 354. As a result, the second transport passage portion from the suction tube 79 to the temporary storage chamber 354 is filled with the liquid.
(Step 3)
The computer 90 opens the second valve 332 to allow the measuring chamber 351 to communicate with the vaporizing chamber 352 and the processing chamber 321 and sucks air in the measuring chamber 351.
(Step 4)
After a lapse of a predetermined time, the computer 90 closes the second valve 332. As a result, the measuring chamber 351 is set to a predetermined vacuum pressure.
(Step 5)
The computer 90 opens the first valve 331. As a result, the liquid in the container 20 is sucked into the measuring chamber 351. As described above, since the suction tube 79 and the subsequent first transport passage portion to the temporary storage chamber 354 are filled with the liquid, no air enters the measuring chamber 351, and the predetermined amount of the liquid is reliably filled into the measuring chamber 351.
(Step 6)
The computer 90 closes the first valve 331 after a predetermined time. This time is set to the time required for completely or substantially completely filing the measuring chamber 351 with the liquid.
(Step 7)
The computer 90 opens the second valve 332. As a result, the liquid in the measuring chamber 351 is drawn by the vacuum of the processing chamber 321 and the vaporizing chamber 352 and vaporized into a gas in the vaporizing chamber 352, and the gas is supplied to the processing chamber 321. Through the steps described above, the predetermined amount (corresponding to the volume of the measuring chamber) of the liquid is gasified, supplied to the processing chamber 321, and utilized for the sterilization process in the chamber.

The amount of the liquid supplied to the processing chamber 321 can be adjusted by repeating steps 4 to 7 described above after step 7.
(Step 8)
When the predetermined amount of the liquid is supplied through the process described above, the computer 90 drives the driving part to pull up the suction tube 79 from the liquid and keeps the suction tube 79 out of contact with the liquid.
(Step 9)
The computer 90 opens the third valve 333, drives the first pump 361 to suck the atmosphere, and returns to container 20 the liquid remaining in the second transport passage 312, the suction tube 79, and the first transport passage 311 between the first branching portion 341 and the first valve 331.

(Step 10)

After a lapse of a predetermined time, the computer 90 closes the third valve 333 and stops the first pump 361.

(Step 11)

The computer 90 closes the second valve 332.

(Step 12)

The computer 90 opens the first valve 331 and sucks the liquid remaining on the upstream side of the first valve 331, for example, the liquid remaining between the first branching portion 341 and the first valve 331, into the measuring chamber 351.

(Step 13)

The computer 90 closes the first valve 331 after a lapse of a predetermined time.

(Step 14)

The computer 90 opens the second valve 332. As a result, the liquid in the measuring chamber 351 is supplied to the processing chamber 321.

(Step 15)

The computer 90 closes the second valve 332 after a predetermined time. This time is set to the time required for completely sucking the liquid or gas remaining in the vaporizing chamber 352 etc. into the processing chamber 321.

As described above, according to the measuring unit 301 of the third embodiment, all the liquid remaining in the temporary storage chamber 354 and the second transport passage 312 is returned to the container.

3.4: Fourth Embodiment

The measuring unit 401 of a fourth embodiment will be described.

3.4.1: Structure

Figure 15:
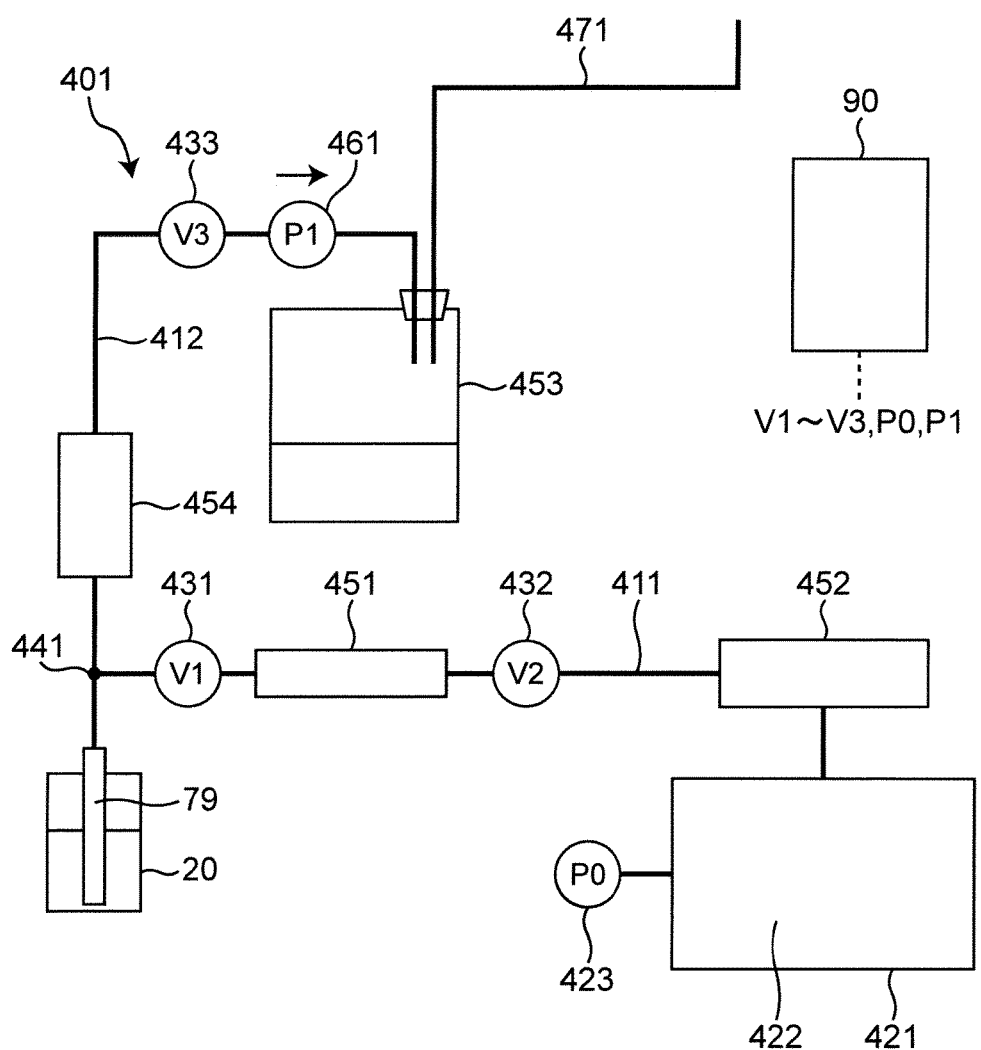
FIG. 15 is a block diagram of a structure of a measuring unit of a fourth embodiment incorporated in the liquid supplying system according to the present invention.

As shown in FIG. 15, the measuring unit 401 of the fourth embodiment has a first transport passage 411 and a second transport passage 412 for transporting a liquid. The first transport passage 411 has one end connected to the upper end of the suction tube 79 and the other end connected to the processing chamber 421. The processing chamber 421 is, for example, a sterilization chamber of a gas sterilization apparatus and is connected to a vacuum pump 423 so that a space 422 in the processing chamber 421 can be made vacuum. Although not shown, the processing chamber 421 is provided with various instruments (e.g., a pressure detector, a temperature detector) necessary for properly managing the sterilization process.

The first transport passage 411 is provided with a first valve 431, a measuring chamber 451, a second valve 432, and a vaporizing chamber 452 in order from the suction tube 79 toward the processing chamber 421. The first transport passage 411 has a branching portion 441 between the first valve and the suction tube 79. The second transport passage 412 has one end connected to the branching portion 441 and the other end connected to a waste liquid storage chamber 453 with a temporary storage chamber 454, a third valve 433, and a pump 461 arranged between the branching portion 441 and the waste liquid storage chamber 453. The inside of the waste liquid storage chamber 453 is opened to the atmosphere via an exhaust pipe 471.

For each of the first to third valves 431 to 433 described above, an electromagnetic valve is suitably used. The vacuum pump 423 and the first to third valves 431 to 433 are connected to the computer 90 and are configured to operate based on an output of the computer 90

3.3.2: Operation

Figure 16:
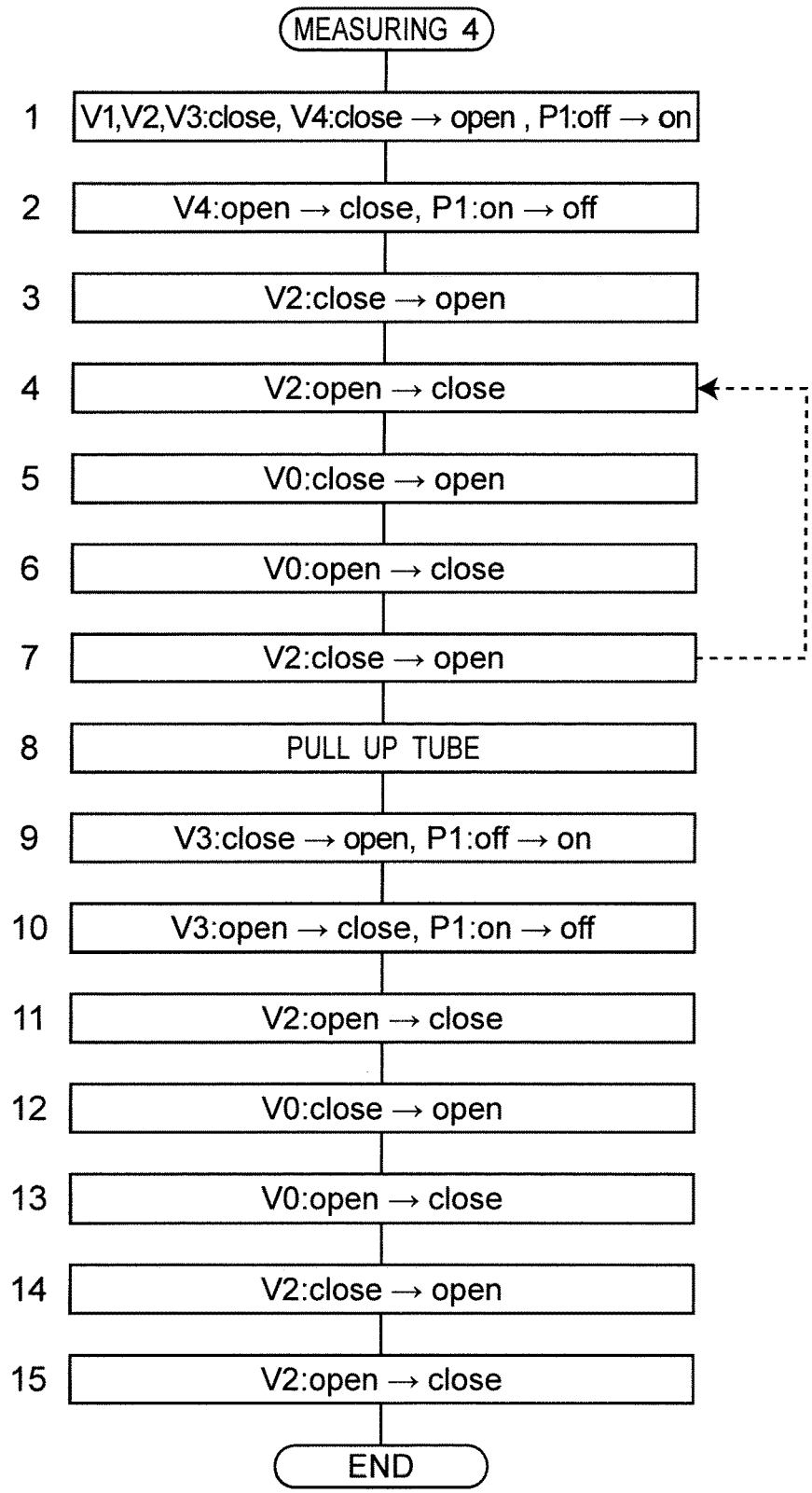
FIG. 16 is a flowchart of an operation of the measuring unit shown in FIG. 15.

An operation of the measuring unit 401 will be described with reference to FIG. 16.

Step 1

When detecting that the tip of the suction tube 79 inserted into the container 20 has reached the container bottom surface or the vicinity thereof, the computer 90 closes the first and second valves 431, 432 and opens the third valve 433. The computer 90 also drives the pump 461. As a result, the liquid in the container 20 is sucked through the suction tube 79 and supplied to the temporary storage chamber 454.

Step 2

After a lapse of a predetermined time, the computer 90 closes the third valve 333 and stops the pump 461. The predetermined time in this case is set such that a predetermined amount of the liquid is filled into the temporary storage chamber 454. As a result, the second transport passage portion from the suction tube 79 to the temporary storage chamber 454 is filled with the liquid.

Step 3

The computer 90 opens the second valve 432 to allow the measuring chamber 451 to communicate with the vaporizing chamber 452 and the processing chamber 421 and sucks air in the measuring chamber 451.

Step 4

After a lapse of a predetermined time, the computer 90 closes the second valve 432. As a result, the measuring chamber 451 is set to a predetermined vacuum pressure.

Step 5

The computer 90 opens the first valve 431. As a result, the liquid in the container 20 is sucked into the measuring chamber 451. As described above, since the suction tube 79 and the subsequent first transport passage portion to the temporary storage chamber 454 are filled with the liquid, no air enters the measuring chamber 451, and the predetermined amount of the liquid is reliably filled into the measuring chamber 451.

Step 6

The computer 90 closes the first valve 431 after a predetermined time. This time is set to the time required for completely or substantially completely filing the measuring chamber 451 with the liquid.

Step 7

The computer 90 opens the second valve 432. As a result, the liquid in the measuring chamber 451 is drawn by the vacuum in the processing chamber 421 and the vaporizing chamber 452 and vaporized into a gas in the vaporizing chamber 452, and the gas is supplied to the processing chamber 421. Through the steps described above, the predetermined amount (corresponding to the volume of the measuring chamber) of the liquid is gasified, supplied to the processing chamber 421, and utilized for the sterilization process in the chamber.

The amount of liquid supplied to the processing chamber 421 can be adjusted by repeating steps 4 to 7 after step 7.

Step 8

When the predetermined amount of the liquid is supplied through the process described above, the computer 90 drives the driving part to pull up the suction tube 79 from the liquid and keeps the suction tube 79 out of contact with the liquid.

Step 9

The computer 90 opens the third valve 333, drives the pump 461 to suck the atmosphere, and returns the liquid remaining in the second transport passage 412 and the suction tube 79 to the container 20.

Step 10

After a lapse of a predetermined time, the computer 90 closes the third valve 333 and stops the pump 461.

Step 11

The computer 90 closes the second valve 432.

Step 12

The computer 90 opens the first valve 431 and sucks the liquid remaining on the upstream side of the first valve 431, for example, the liquid remaining between the branching portion 441 and the first valve 431, into the measuring chamber 451.

Step 13

The computer 90 closes the first valve 431 after a lapse of a predetermined time.

Step 14

The computer 90 opens the second valve 432. As a result, the liquid in the measuring chamber 451 is supplied to the processing chamber 421.

Step 15

The computer 90 closes the second valve 432 after a predetermined time. This time is set to the time required for completely sucking the liquid or gas remaining in the vaporizing chamber 452 etc. into the processing chamber 421.

As described above, according to the measuring unit 401 of the fourth embodiment, all the liquid remaining in the temporary storage chamber 454 and the second transport passage 412 is returned to the container.

EXPLANATIONS OF LETTERS OR NUMERALS

1 liquid supplying system
2 supplying unit
10 housing
11 front wall
12 opening
13 doors
14 metal piece
15 magnet
16 base
20 liquid container
21 main body
22 central axis
23 lid
24 ceiling wall
25 central area
26 shoulder portion
27 bottom portion
30 container receiving part
31 lower support portion
32 upper support portion
33 table
34 lower half-cylindrical wall
35 upper half-cylindrical wall
36 vertical portion
37 cylindrical wall
38 projection
39 vertical axis
40 container housing chamber
41 side wall
42 back wall
43 ceiling wall
44 window
45 extended side wall
46 extended back wall
47 gap
50 first moving mechanism
51 fixed bracket (first fixed part)
52 driving part (first driving part)
53 ball screw
54 nut
55 movable bracket (first movable part)
56 vertical guide (rotation preventing means)
57 hole
58 hollow piercing needle
59 steeple portion
60 lock mechanism
61 lock plate
62 first portion
63 second portion
64 third portion (engaging part)
65 engaged part
70 second moving mechanism
71 fixed bracket (second fixed part)
72 driving part (second driving part)
73 ball screw
74 nut
75 movable bracket (second movable part)
76 through-hole
77 guide rod
78 through-hole
79 suction tube
80 holder
81, 82, 83 detector
84, 85 detector
90 computer (control part)
101 measuring unit (first embodiment)
111 first transport passage
112 second transport passage
113 third transport passage
114 fourth transport passage
121 processing chamber 122 space
123 vacuum pump (first depressurizing means)
131 first valve
132 second valve
133 third valve
134 fourth valve
135 fifth valve
141 first branching portion
142 second branching portion
143 third branching portion
151 measuring chamber
152 vaporizing chamber
153 waste liquid storage chamber
154 temporary storage chamber
201 measuring unit (second embodiment)
211 first transport passage
212 second transport passage
213 third transport passage
214 fourth transport passage
221 processing chamber
222 space
223 vacuum pump (first depressurizing means)
231 first valve
232 second valve
233 third valve
234 fourth valve
235 fifth valve
241 first branching portion
242 second branching portion
251 measuring chamber
252 vaporizing chamber
253 waste liquid storage chamber
301 measuring unit (third embodiment)
311 first transport passage
312 second transport passage
313 third transport passage
321 processing chamber
322 space
323 vacuum pump (first depressurizing means)
331 first valve
332 second valve
333 third valve
334 fourth valve
341 first branching portion
342 second branching portion
351 measuring chamber
352 vaporizing chamber
353 waste liquid storage chamber
354 temporary storage chamber
361 pump
362 pump
371 exhaust pipe
401 measuring unit (fourth embodiment)
411 first transport passage
412 second transport passage
421 processing chamber
422 space
423 vacuum pump (first depressurizing means)
431 first valve
432 second valve
433 third valve
441 branching portion
451 measuring chamber
452 vaporizing chamber
453 waste liquid storage chamber
454 temporary storage chamber
461 pump
471 exhaust pipe

The invention claimed is:

1. A liquid supplying system comprising:
a processing chamber having a space of a predetermined volume;
a first depressurizing means depressurizing the space of the processing chamber;
a container containing a liquid;
a measuring chamber measuring the liquid;
a first passage connecting the container and the processing chamber through the measuring chamber;
a first valve disposed on the first passage between the container and the measuring chamber;
a second valve disposed on the first passage between the measuring chamber and the processing chamber; and
a control part controlling the depressurizing means, the first valve, and the second valve, wherein
the control part includes
a) a first means executing a first process of driving the first depressurizing means to depressurize the processing chamber so as to form a negative pressure in the processing chamber with the second valve closed,
b) a second means executing a second process of opening the second valve with the first valve closed so as to introduce the negative pressure of the processing chamber into the measuring chamber,
c) a third means executing a third process of closing the second valve with the first valve closed so as to retain the negative pressure introduced into the measuring chamber,
d) a fourth means executing a fourth process of opening the first valve with the second valve closed so as to suck the liquid from the container into the measuring chamber by using the negative pressure of the measuring chamber,
e) a fifth means executing a fifth process of opening the second valve with the first valve closed so as to suck the liquid in the measuring chamber into the processing chamber by using a vacuum in the processing chamber,
f) a branching portion disposed on the first passage between the container and the first valve
g) a second passage having one end connected to the branching portion,
h) a second depressurizing means connected to the other end of the second passage,
i) a temporary storage chamber and a third valve disposed on the second passage in this order from the one end toward the other end, and
j) a sixth means executing a sixth process of driving the second depressurizing means with the third valve opened before execution of the first process so as to suck the liquid into the second passage portion from the container to the temporary storage chamber.

2. The liquid supplying system according to claim 1, comprising a seventh means executing a seventh process of returning to the container the liquid remaining in the second passage portion from the container to the third valve after the fifth process.

3. The liquid supplying system according to claim 1, comprising
a third valve disposed on the second passage, wherein
the liquid supplying system comprises
a seventh means executing a seventh process of driving the second depressurizing means with the third valve opened before execution of the first process so as to suck the liquid into the second passage portion from the container to the third valve.

4. The liquid supplying system according to claim 3, comprising an eighth means executing an eighth process of returning to the container the liquid remaining in the second passage portion from the container to the third valve after the fifth process.

5. The liquid supplying system according to claim 1, comprising a means repeating the second to fifth processes twice or more.

6. A method for driving a liquid supplying system including
- a processing chamber having a space of a predetermined volume,
- a first depressurizing means depressurizing the space of the processing chamber,
- a container containing a liquid,
- a measuring chamber measuring the liquid,
- a first passage connecting the container and the processing chamber through the measuring chamber,
- a first valve disposed on the first passage between the container and the measuring chamber,
- a second valve disposed on the first passage between the measuring chamber and the processing chamber, and
- a control part controlling the first depressurizing means, the first valve, and the second valve,
- the method comprising:
- a) a first step of executing a first process of driving the first depressurizing means to depressurize the processing chamber so as to form a negative pressure in the processing chamber with the second valve closed;
- b) a second step of executing a second process of opening the second valve with the first valve closed so as to introduce the negative pressure of the processing chamber into the measuring chamber;
- c) a third step of executing a third process of closing the second valve with the first valve closed so as to retain the negative pressure introduced into the measuring chamber;
- d) a fourth step of executing a fourth process of opening the first valve with the second valve closed so as to suck the liquid from the container into the measuring chamber by using the negative pressure of the measuring chamber;
- e) a fifth step of executing a fifth process of opening the second valve with the first valve closed so as to suck the liquid in the measuring chamber into the processing chamber by using a vacuum in the processing chamber,
- wherein the liquid supplying system further including
- a branching portion disposed on the first passage between the container and the first valve
- a second passage having one end connected to the branching portion,
- a second depressurizing means connected to the other end of the second passage,
- a temporary storage chamber and a third valve disposed on the second passage between the one and the other ends of the second passage, the temporary storage chamber and the third valve being disposed in this order from the one end toward the other end of the second passage, and
- the method further comprising:
- f) a sixth step of driving the second depressurizing means with the third valve opened before execution of the first process so as to suck the liquid into the second passage portion from the container to the temporary storage chamber.

7. The method for driving a liquid supplying system according to claim 6, comprising a seventh step of executing a seventh process of returning to the container the liquid remaining in the second passage portion from the container to the third valve after the fifth process.

8. The method for driving a liquid supplying system according to claim 6, wherein
- the liquid supplying system includes
- a third valve on the second passage, and wherein
- the method comprises
- f) a seventh step of executing a seventh process of driving the second depressurizing means with the third valve opened before execution of the first process so as to suck the liquid into the second passage portion from the container to the third valve.

9. The method for driving a liquid supplying system according to claim 8, comprising an eighth step of executing an eighth process of returning to the container the liquid remaining in the second passage portion from the container to the third valve after the fifth process.

10. The method for driving a liquid supplying system according to claim 6, wherein the second to fifth processes are repeated twice or more.

* * * * *